(12) United States Patent
Bolus

(10) Patent No.: US 12,329,497 B1
(45) Date of Patent: Jun. 17, 2025

(54) PROCESSING AND ANALYZING BIOMETRIC DATA

(71) Applicant: Huxley Medical, Inc., Atlanta, GA (US)

(72) Inventor: Nicholas Bradford Bolus, Birmingham, AL (US)

(73) Assignee: HUXLEY MEDICAL, INC., Atlanta, GA (US)

( * ) Notice: Subject to any disclaimer, the term of this patent is extended or adjusted under 35 U.S.C. 154(b) by 0 days.

(21) Appl. No.: 18/822,043

(22) Filed: Aug. 30, 2024

Related U.S. Application Data

(63) Continuation of application No. 18/299,539, filed on Apr. 12, 2023, now Pat. No. 12,076,117, which is a continuation of application No. 17/833,894, filed on Jun. 6, 2022, now Pat. No. 11,660,005.

(60) Provisional application No. 63/196,778, filed on Jun. 4, 2021.

(51) Int. Cl.
*A61B 5/02* (2006.01)
*A61B 5/1455* (2006.01)
*A61B 5/318* (2021.01)

(52) U.S. Cl.
CPC .............. *A61B 5/02* (2013.01); *A61B 5/1455* (2013.01); *A61B 5/318* (2021.01)

(58) Field of Classification Search
CPC .......... A61B 5/02; A61B 5/1455; A61B 5/318
See application file for complete search history.

(56) References Cited

U.S. PATENT DOCUMENTS

| | | |
|---|---|---|
| 112,102 A | 2/1871 | Whittemore |
| 142,988 A | 9/1873 | Bbobstotf |
| 162,627 A | 4/1875 | Coyle |
| 210,034 A | 11/1878 | Higgins et al. |
| 213,007 A | 3/1879 | Thayee |
| 825,537 A | 7/1906 | Macmillan |

(Continued)

FOREIGN PATENT DOCUMENTS

| | | |
|---|---|---|
| AU | 2015253309 B2 | 2/2021 |
| CN | 218978894 U | 5/2023 |

(Continued)

OTHER PUBLICATIONS

Mendelson, et al., Noninvasive Pulse Oximetry Utilizing Skin Reflectance Photoplethysmography, IEEE Transactions on Biomedical Engineering, Oct. 1988, 8 pages, vol. 35 No. 10.

(Continued)

*Primary Examiner* — Jonathan T Kuo
(74) *Attorney, Agent, or Firm* — Husch Blackwell LLP; Bryan D. Stewart

(57) ABSTRACT

The present disclosure relates to a cardiorespiratory analysis system that includes, in at least one embodiment, a conformal patch with a compressible viscoelastic interface and an array of sensors, including, but not limited to a photoplethysmography (PPG) sensor, a 3-axis accelerometer, and an electrocardiogram (ECG) sensor. In at least one embodiment, the system includes a microcontroller wired to the array of sensors. According to at least one embodiment, the system uses computing techniques to derive features from the array of sensors and determines one or cardiorespiratory characteristics of a patient based on the derived features.

19 Claims, 8 Drawing Sheets

(56) References Cited

U.S. PATENT DOCUMENTS

| | | |
|---|---|---|
| 1,248,586 A | 12/1917 | Wood |
| 3,052,232 A | 9/1962 | Zworykin et al. |
| 3,195,535 A | 7/1965 | Westermann |
| 3,638,642 A | 2/1972 | Heflin, Sr. |
| 4,104,728 A | 8/1978 | Kasubuchi |
| 4,121,573 A | 10/1978 | Crovella et al. |
| 4,957,109 A | 9/1990 | Groeger et al. |
| 5,016,202 A | 5/1991 | Seibel et al. |
| 5,033,202 A | 7/1991 | Chen |
| 5,050,613 A | 9/1991 | Newman et al. |
| 5,251,286 A | 10/1993 | Wiener et al. |
| 5,307,818 A | 5/1994 | Segalowitz |
| 5,546,811 A | 8/1996 | Rogers et al. |
| 5,633,711 A | 5/1997 | Nelson et al. |
| 5,672,830 A | 9/1997 | Rogers et al. |
| 5,734,470 A | 3/1998 | Rogers et al. |
| 5,800,478 A | 9/1998 | Chen et al. |
| 5,812,261 A | 9/1998 | Nelson et al. |
| 5,951,881 A | 9/1999 | Rogers et al. |
| 5,982,482 A | 11/1999 | Nelson et al. |
| 6,052,185 A | 4/2000 | Banet et al. |
| 6,069,703 A | 5/2000 | Banet et al. |
| 6,148,127 A | 11/2000 | Adams et al. |
| 6,150,668 A | 11/2000 | Bao et al. |
| 6,169,831 B1 | 1/2001 | Adams et al. |
| 6,181,852 B1 | 1/2001 | Adams et al. |
| 6,192,177 B1 | 2/2001 | Amundson et al. |
| 6,252,253 B1 | 6/2001 | Bao et al. |
| 6,256,100 B1 | 7/2001 | Banet et al. |
| 6,275,629 B1 | 8/2001 | Eggleton et al. |
| 6,285,812 B1 | 9/2001 | Amundson et al. |
| 6,303,182 B1 | 10/2001 | Eggleton et al. |
| 6,307,988 B1 | 10/2001 | Eggleton et al. |
| 6,329,226 B1 | 12/2001 | Jones et al. |
| 6,337,761 B1 | 1/2002 | Rogers et al. |
| 6,351,585 B1 | 2/2002 | Amundson et al. |
| 6,363,096 B1 | 3/2002 | Dodabalapur et al. |
| 6,370,300 B1 | 4/2002 | Eggleton et al. |
| 6,410,416 B1 | 6/2002 | Dodabalapur et al. |
| 6,427,040 B1 | 7/2002 | Ahuja et al. |
| 6,438,277 B1 | 8/2002 | Eggleton et al. |
| 6,529,676 B2 | 3/2003 | Eggleton et al. |
| 6,589,629 B1 | 7/2003 | Bao et al. |
| 6,655,286 B2 | 12/2003 | Rogers |
| 6,719,868 B1 | 4/2004 | Schueller et al. |
| 6,736,985 B1 | 5/2004 | Bao et al. |
| 6,743,982 B2 | 6/2004 | Biegelsen et al. |
| 6,753,131 B1 | 6/2004 | Rogers et al. |
| 6,769,769 B2 | 8/2004 | Podoleanu et al. |
| 6,778,734 B2 | 8/2004 | Baldwin et al. |
| 6,795,198 B1 | 9/2004 | Fuchs et al. |
| 6,829,415 B2 | 12/2004 | Kroupenkine et al. |
| 6,856,731 B2 | 2/2005 | Rogers et al. |
| 6,895,688 B2 | 5/2005 | Acharya et al. |
| 6,927,860 B2 | 8/2005 | Podoleanu et al. |
| 6,943,998 B2 | 9/2005 | Shimazawa et al. |
| 6,946,332 B2 | 9/2005 | Loo et al. |
| 7,110,646 B2 | 9/2006 | Eggleton et al. |
| 7,139,478 B2 | 11/2006 | Eggleton et al. |
| 7,195,733 B2 | 3/2007 | Rogers et al. |
| 7,199,699 B1 | 4/2007 | Gidge |
| 7,229,541 B2 | 6/2007 | Hara et al. |
| 7,330,213 B2 | 2/2008 | Yamamoto |
| 7,417,741 B2 | 8/2008 | Podoleanu et al. |
| 7,439,096 B2 | 10/2008 | Baldwin et al. |
| 7,521,292 B2 | 4/2009 | Rogers et al. |
| 7,557,367 B2 | 7/2009 | Rogers et al. |
| 7,704,684 B2 | 4/2010 | Rogers et al. |
| 7,705,280 B2 | 4/2010 | Nuzzo et al. |
| 7,943,491 B2 | 5/2011 | Nuzzo et al. |
| 8,372,726 B2 | 2/2013 | De Graff et al. |
| 8,734,339 B2 | 5/2014 | Rao et al. |
| 9,061,494 B2 | 6/2015 | Rogers et al. |
| 9,119,533 B2 | 9/2015 | Ghaffari |
| 9,247,637 B2 | 1/2016 | Hsu |
| 9,372,123 B2 | 6/2016 | Li et al. |
| 9,545,285 B2 | 1/2017 | Ghaffari et al. |
| 9,554,850 B2 | 1/2017 | Lee et al. |
| 9,579,040 B2 | 2/2017 | Rafferty et al. |
| 9,613,911 B2 | 4/2017 | Rogers et al. |
| 9,622,680 B2 | 4/2017 | Ghaffari et al. |
| 9,629,586 B2 | 4/2017 | Ghaffari et al. |
| 9,702,839 B2 | 7/2017 | Ghaffari et al. |
| 9,704,908 B2 | 7/2017 | Graff et al. |
| 9,706,647 B2 | 7/2017 | Hsu et al. |
| 9,723,122 B2 | 8/2017 | Ghaffari et al. |
| 9,723,711 B2 | 8/2017 | Elolampi et al. |
| 9,744,145 B1 | 8/2017 | Liu et al. |
| 9,746,829 B2 | 8/2017 | Stranczl et al. |
| 9,750,421 B2 | 9/2017 | Ghaffari et al. |
| 9,757,050 B2 | 9/2017 | Ghaffari et al. |
| 9,810,623 B2 | 11/2017 | Ghaffari et al. |
| 9,833,190 B2 | 12/2017 | Ghaffari et al. |
| 9,894,757 B2 | 2/2018 | Arora et al. |
| 9,899,330 B2 | 2/2018 | Dalal et al. |
| 9,949,691 B2 | 4/2018 | Huppert et al. |
| 10,024,743 B2 | 7/2018 | Gaboriault et al. |
| 10,032,709 B2 | 7/2018 | Rafferty et al. |
| 10,161,737 B2 | 12/2018 | Pegan et al. |
| 10,186,546 B2 | 1/2019 | De Graff et al. |
| 10,192,830 B2 | 1/2019 | Rogers et al. |
| 10,582,618 B2 | 3/2020 | Coleman et al. |
| 10,898,084 B2 | 1/2021 | Khine et al. |
| 11,207,002 B2 | 12/2021 | Khine et al. |
| 2002/0180605 A1 | 12/2002 | Ozguz et al. |
| 2005/0096513 A1 | 5/2005 | Ozguz et al. |
| 2014/0275845 A1* | 9/2014 | Eagon ............... A61B 5/6826 600/301 |
| 2014/0275888 A1* | 9/2014 | Wegerich ............ A61B 5/053 600/324 |
| 2015/0351689 A1 | 12/2015 | Adams et al. |
| 2016/0302674 A1* | 10/2016 | Moyer ............... A61B 5/02416 |
| 2016/0313176 A1 | 10/2016 | Lee |
| 2017/0079144 A1 | 3/2017 | Coleman et al. |
| 2017/0156623 A1 | 6/2017 | Chu et al. |
| 2017/0347894 A1 | 12/2017 | Bhushan et al. |
| 2018/0177459 A1 | 6/2018 | Eletr et al. |
| 2019/0069788 A1 | 3/2019 | Coleman et al. |
| 2019/0113326 A1 | 4/2019 | Pegan et al. |
| 2019/0142625 A1 | 5/2019 | Goff et al. |
| 2020/0069193 A1 | 3/2020 | Khine et al. |
| 2020/0255791 A1 | 8/2020 | Yeo et al. |
| 2021/0000042 A1 | 1/2021 | Birru et al. |
| 2021/0161405 A1 | 6/2021 | Khine et al. |
| 2022/0009764 A1 | 1/2022 | Zhou et al. |
| 2022/0280066 A1 | 9/2022 | Chu et al. |

FOREIGN PATENT DOCUMENTS

| | | |
|---|---|---|
| EP | 3137038 B1 | 12/2020 |
| EP | 3083248 B1 | 4/2022 |
| EP | 3877830 A1 | 8/2022 |
| EP | 3673797 A1 | 6/2024 |
| WO | 2015095836 A3 | 11/2015 |
| WO | 2015179320 A1 | 11/2015 |
| WO | 2015179322 A3 | 3/2016 |
| WO | 2017220526 A1 | 12/2017 |
| WO | 2020092747 A1 | 5/2020 |
| WO | 2020097505 A1 | 5/2020 |
| WO | 2020228724 A1 | 11/2020 |
| WO | 2021055496 A1 | 3/2021 |
| WO | 2021142121 A1 | 7/2021 |

OTHER PUBLICATIONS

Rusch, et al., Alternate Pulse Oximetry Algorithms for Sp02 Computation, University of South Florida, 1994, 2 pages.

Rusch, et al., Signal Processing Methods for Pulse Oximetry, Comput. Biol. Med., Oct. 1995, 17 pages, vol. 26 No. 2.

Dassel, et al., Effect of location of the sensor on reflectance pulse oximetry, British Journal of Obstetrics and Gynaecology, Aug. 1997, pp. 910-916, vol. 104.

(56) References Cited

OTHER PUBLICATIONS

Goldman, et al., Masirno Signal Extraction Pulse Oximetry, Journal of Clinical Monitoring and Computing, Jan. 2000, 9 pages, vol. 16, Kluwer Academic Publishers, Netherlands.
Clifford, et al., Signal Processing Methods for Heart Rate Variability, St. Cross College, 2002, 244 pages.
Graybeal, et al., Adaptive Filtering and Alternative Calculations Revolutionizes Pulse Oximetry Sensitivity and Specificity During Motion and Low Perfusion, IEEE EMBS, Sep. 2004, 4 pages.
Johnston, Development of a Signal Processing Library for Extraction of SpO2, HR, HRV, and RR from Photoplethysmographic Waveforms, Worcester Polytechnic Institute, 2006, 148 pages.
Morillo, et al., Monitoring and Analysis of Cardiorespiratory and Snoring Signals by using an Accelerometer, IEEE EMBS, Aug. 2007, 4 pages.
Nilsson, et al., Combined photoplethysmographic monitoring of respiration rate and pulse: a comparison between different measurement sites in spontaneously breathing subjects, Acta Anaesthesiol Scand, 2007, 8 pages, vol. 51.
Sola, et al., On the reliability of pulse oximetry at the sternum, IEEE EMBS, Aug. 2007, 1 page.
Hung, et al., Estimation of Respiratory Waveform Using an Accelerometer, IEEE ISBI, 2008, 4 Pages.
Tilmanne, et al., Algorithms for sleep-wake identification using acligraphy: a comparative study and new results, European Sleep Research Society, Sep. 2008, 14 pages.
Barker, Signal Extraction Technology, Nov. 30, 2009, 45 pages.
Etemadi, et al., Non-Invasive Assessment of Cardiac Contractility on a Weighing Scale, IEEE EMBS, Sep. 2009, 4 pages.
Jensen, Signal Processing of Nano Sensor Data, Kongens Lyngby, Mar. 2009, 127 pages.
Jensen, et al., Independent Component Analysis Applied to Pulse Oximelry in the Estimation of the Arterial Oxygen Saturation {SpO2}—a Comparative Study, IEEE EMBS, Sep. 2009, 7 pages.
Vetter, et al., Frequency Domain SpO2 Estimation Based on Multichannet Photoplethysmographic Measurements the Sternum, IFMBE Proceedings, 2009, 4 pages, vol. 25.
Bsoul, et al., Real-Time Sleep Quality Assessment Using Single-Lead ECG and Multi-Stage SVM Classifier, IEEE, Sep. 2010, 4 pages, Buenos Aires.
Inan, et al., Evaluating the Lower-Body Electromyogram Signal Acquired from the Feet as a Noise Reference for Standing Ballistocardiogram Measurements, IEEE Transactions on Information Technology in Biomedicine, Sep. 2010, 9 pages, vol. 14 No. 5.
Morillo, et al., An Accelerometer-Based Device for Sleep Apnea Screening, IEEE Transactions on Information Technology in Biomedicine, Mar. 2010, 9 pages, vol. 10 No. 2.
Pandia, et al., Motion Artifact Cancellation to Obtain Heart Sounds From a Single Chestworn Accelerometer, IEEE ICASSP, 2010, 4 pages.
Tavakolian, Characterization and Analysis of Seismocardiogram for Estimation of Hemodynamic Parameters, Simon Fraser University, Fall 2010, 217 pages.
Bsoul, et al., Apnea MedAssist Real-time Sleep Apnea Monitor Using Single-Lead ECG, IEEE Transactions on Information Technology in Biomedicine, May 2011, 12 pages, vol. 15.
Li, et al., Principle Component Analysis on Photoplethysmograms: Blood Oxygen Saturation Estimation and Signal Segmentation, IEEE EMBS, Sep. 2011, 4 pages.
Sola, et al., Chest Pulse-Wave Velocity: A Novet Approach to Assess Arterial Stiffness, IEEE Transactions on Biomedical Engineering, Jan. 2011, 9 pages, vol. 58 No. 1.
Younes Sleep Technologies. "Traditional 510(k) Summary K112102 Michelle Sleep Scoring System." Oct. 16, 2011, 16 pages.
Castiglioni, et al., Seisrnocarcliography While Sleeping at High Altitude, IEEE EMBS, Aug. 2012, 4 pages.
Clifford, et al., Signal quality in cardiorespiratory monitoring, Physiol. Meas. 33 E01, 2012, 6 pages.

Haahr, et al., An Electronic Patch for Wearable Health Monitoring by Reflectance Pulse Oximetry, IEEE Transactions on Biomedical Circuits and Systems, Feb. 2012, 9 pages, vol. 6 No. 1.
Pandia, et al., Extracting respiratory information from seismocardiogram signals acquired on the chest using a miniature accelerometer, Physiological Measurement, Sep. 2012, 19 pages, vol. 33.
Di Rienzo, et al., Wearable seismocardiography: Towards a beat-by-beat assessment of cardiac mechanics in ambulant subjects, Autonomic Neuroscience: Basic and Clinical, Apr. 2013, 10 pages.
Pandia, et al., A Frequency Domain Analysis of Respiratory Variations in the Seismocardiogram Signal, IEEE EMBS, Jul. 2013, 4 pages.
He, et al., Secondary Peak Detection of PPG Signal for Continuous Cuffless Artenal Blood Pressure Measurement, IEEE Transactions on Instrumentation and Measurement, Jun. 2014, 9 pages.
Inan, et al., Ballistocarcliography and Seismocarcliography: A Review of Recent Advances, IEEE Journal of Biomedical and Heal TH Informatics, 2014, 30 pages.
Nara, et al., Novet Notch Detection Algorithm for Detection of Dicrotic Notch in PPG Signals, International Journal of Computer Applications, Jan. 2014, 5 pages, vol. 86 No. 17.
Broser, et al., Ambient and Unobtrusive Cardiorespiratory Monitoring Techniques, IEEE Reviews in Biomedical Engineering, 2015, 14 pages, vol. 8.
Budidha, et al., Investigation of photoplethysmography and arterial blood oxygen saturation from the ear-canal and the finger under conditions of artificially induced hypothermia, IEEE Engineering in Medicine and Biology Society Conference, Aug. 2015, 5 pages.
Fonseca, et al., Sleep stage classification with ECG and respiratory effort, Physiological Measurement, 2015, 15 pages, vol. 36.
U.S. Department of Health & Human Services. "Letter re: K142988, Trade/Device Name: Sleepware G3 . . . " Received by Respironics, Inc., Mar. 16, 2015, 8 pages.
Chreiteh, Investigation of Sternal Photoplelhysmography—Design of a Vital Sign Patch, Technical University of Denmark, Mar. 2016, 187 pages.
Etemadi, et al., A Wearable Patch to Enable Long-Term Monitoring of Environmental, Activity and Hemodynamics Variables, IEEE Transactions on Biomedical Circuits and Systems, 2016, 9 pages.
Javaid, et al., Quantification of Posture Induced Changes in Wearable Seismocardiogram Signals for Heart Failure Patients, Computing in Cardiology, 2016, 4 pages, vol. 43.
Zheng, et al., Low Ferfusion Algorithm used in Wearable Oximeter and Hardware Acceleration, IEEE, 2016, 5 pages.
Carek, et al., SeismoWatch: Wearable Cuffless Blood Pressure Monitoring Using Pulse Transit Time, Proc. ACM Interact. Mob. Wearable Ubiquitous Technol. 1, 3, Article 40, Sep. 2017, 16 pages.
Etemadi, et al., Wearable Ballistocardiogram and Seismocardiogram Systems for Health and Performance, Press. J Appl Physiol, Aug. 2017, 35 pages.
Inan, Wearable Sensing of Left Ventncular Function, Spring International Publishing, Mobile Health, 2017, 23 pages.
Javaid, et at, Quantifying and Reducing Motion Artifacts in Wearable Seismocardiogram Measurements during Walking to Assess Left Ventricular Health, IEEE TBME, 2017, 9 pages.
Khosrow-Khavar, et al., Automatic and Robust Delineation of the Fiducial Points of the Seismocardiogram Signal for Noninvasive Estimation of Cardiac Time Intervals, IEEE Transactions On Biomedical Engineering, Aug. 2017, 10 pages, vol. 64. No. 8.
Kramer, et al., Wearable Pulse Oximetry Measurements on the Torso, Arms, and Legs: A Proof of Concept, Military Medicine, 2017, 7 pages.
Shafiq, et al., Data Descriptor: Multimodal chest surface motion data for respiratory and cardiovascular monitoring applications, Scientific Data, Apr. 2017, 12 pages.
Telfer, et al., Wearable Oximeby for Harsh Environments, IEEE, 2017, 4 pages.
U.S. Department of Health & Human Services. "Letter re: K162627, Trade/Device Name: EnsoSleep" Received by EnsoData, Inc., Mar. 31, 2017, 7 pages.
Zakeri, et al., Analyzing Seismocardiogram Cycles to Identify the Respiratory Phases, IEEE Transactions on Biomedical Engineering, Aug. 2017, 7 pages, vol. 64 No. 8.

(56) References Cited

OTHER PUBLICATIONS

Bicen, et al., A Signal Quality Index for Ballistocardiogram Recordings based on Electrocardiogram RR Intervals and Matched Filtering, IEEE EMBS International Conference on Biomedical & Health Informatics (BHI), Mar. 2018, 4 pages, Las Vegas.

Biometrics, et al., Medical electrical equipment—Part 2-61: Requirements for basic safety and essential performance of pulse oximeter equipment, International Standard, 2018, 100 pages, vol. 2.0, Geneva.

Hung, Central Sleep Apnea Detection Using an Accelerometer, Association for Computing Machinery, Jun. 2018, 6 pages.

Inan, et al., Novet Wearable Seismocardiography and Machine Learning Algorithms Can Assess Clinical Status of Heart Failure Patients, Circ Heart Fail., 2018, 10 pages.

Jortberg, et al., a novet adhesive biosensor system for detecting respiration, cardiac, and limb movement signals during sleep: validation with polysomnography, Nature and Science of Sleep, 2018, 12 pages, vol. 10.

Liang, et al., Analysis: An optimal filler for short pholoplethysmogram signals, Scientific Data, May 2018, 12 pages.

Schlotthauer, et al., Measuring Complexity of Biomedical Signals, Hindawi Complexity, 2018, 4 pages, vol. 2018.

Sorensen, et al., Definition of Fiducial Points in the Normal Seismocardiogram, Scientific Reports, Oct. 2018, 11 pages.

Boe, et al., Automating sleep stage classification using wireless wearable sensors, npj Digital Medicine, 2019, 9 pages.

Budidha, et al., Photoplethysrnography for Quantitative Assessment of Sympathetic Nerve Activity (SNA) During Cold Stress, Front, Physiol, 9:1863, 2019, 10 pages, doi: 10.3389/fphys.2018.01863.

Choudhary, et al., Automatic Detection of Aortic Valve Opening Using Seismocarcliography in Healthy Individuals, IEEE Journal of Biomedical and Heal TH Informatics, May 2019, 9 pages, vol. 23, No. 3.

Dehkordi, et al., Comparison of Different Methods for Estimating Cardiac Timings: A Comprehensive Multimodal Echocardiography Investigation, Front. Physiol. 10:1057, Aug. 2019, 11 pages.

Gao, et al., Obstructive sleep apnea syndrome detection based on ballistocardiogram via machine learning approach, Mathematical Biosceinces and Engineering, Jun. 2019, 15 pages.

Ha et al., A Chest-Laminated Ultrathin and Stretchable E-Tattoo for the Measurement of Electrocardiogram, Seismocardiogram, and Cardiac Time Intervals, Advanced Science, 2019, 13 pages, vol. 6.

Hartmann, et al., Quantitative Comparison of Photoplethysmographic Waveform Characteristics: Effect of Measurement Site, front. Physiol., Mar. 2019, 8 pages.

Hossein, et al., Accurate Detection of Dobutamineinduced Haemodynamic Changes by Kino-Carcliography: A Randomised Double-Blind Placebo-Controlled Validation study, Scientific Reports, Jul. 2019, 11 pages.

Longmore, et al., A Comparison of Reflective Pholoplelhysmography for Detection of Heart Rate, Blood Oxygen Saturation, and Respiration Rate at Various Anatomical Locations, Sensors, Apr. 2019, 19 pages.

Morra, et al., Modification of the mechanical cardiac performance during end-expiratory voluntary apnea recorded with ballistocardiography and seismocardiography, Physiological Measurement, 2019, 32 pages.

Muthasamy, et al., An Overview of Respiratory Airflow Estimation Techniques: Acoustic vs Non-Acoustic, IEEE International Conference on Signal and Image Processing Applications, Sep. 2019, 5 pages.

Pandey, et al., Pulse Oximeter for Low Sp02 Levet Detection Using Discrete Time Signal Processing Algorithm, Journal of Medical Devices, Jun. 2019, 8 pages, vol. 18.

Taebi, et al., Recent Advances in Seismocardiography, Vibration, 2019, 23 pages, vol. 2.

Tamura, Current progress of photoplethysmography and SP02 for health monitoring, Biomedical Engineering Letters, Feb. 2019, 16 pages, vol. 9.

Tusman, et al., Pholoplelhysmographic characterization of vascular lone mediated changes in arterial pressure: an observational study, Journal of Clinical Monitoring and Computing, 2019, 10 pages, vol. 33.

FDA U.S. Food & Drug Administration. "Letter re: K202142, Trade/Device Name: Sleepware G3" Received by Respironics, Inc., Oct. 29, 2020, 9 pages.

Ganti, et al., Wearable Cuff-less Blood Pressure Estimation at Home via Pulse Transit Time, IEEE Journal of Biomedical and Health Informatics, 2020, 12 pages.

Gupta, et al., Precision wearable accelerometer contact microphones for longitudinal monitoring of mechano-acoustic pardiopulmonary signals, npj Digital medicine, 2020, 8 pages.

Hsu, et al., Screening of obstructive sleep apnea in patients who snore using a patch-type device with electrocardiogram and 3-axis accelerometer, Journal of Clinical Sleep Medicine, 2020, 12 pages.

Klum, et al., Wearable Cardiorespiratory Monitoring Employing a Multimodal Digital Patch Stethoscope: Estimation of ECG, PEP, LVET and Respiration Using a 55 mm Single-Lead ECG and Phonocardiogram, Sensors, Apr. 2020, 21 pages, vol. 20.

Morra, et al., Ballistocardiography and Seismocardiography detect hemodynamic changes during simulated obstructive apnea, Physiological Measurement, 2020, 34 pages.

Munck, et al., Multichannet seismocardiography: an imaging modality for investigating heart vibrations, Physiological Measurement, 2020, 12 pages, vol. 41.

Racape, et al., Influence of sympathetic activation on myocardial contractility measured with ballistocardiography and seismocardiography during sustained end-expiratory apnea, Am J Physiol Regul Integr Comp Physiol, Sep. 2020, 10 pages.

Semiz, et al., Non-Invasive Wearable Patch Utilizing Seismocardiography for Peri-Operative Use in Surgical Patients, IUEEE, 2020, 11 pages.

Skoric, et al., Relationship of the Respiration Waveform to a Chest Worn Inertial Sensor, IEEE, 2020, 4 pages.

FDA U.S. Food & Drug Administration. Letter re: 1<210034, Trade/Device Name: EnsoSleep . . . Received by EnsoData, Inc., May 2021, 24 pages.

Kwon, et al., Recent advances in wearable sensors and portable electronics for sleep monitoring, iScience, May 2021, 16 pages, vol. 24.

"510(k) Premarket Notification." Accessdata.fda.gov, U.S. Department of Health & Human Services, Aug. 22, 2022, https://www.accessdata.fda.gov/scripts/cdrh/cfdocs/cfpmn/pmn.cfm?I.

FDA U.S. Food & Drug Administration. aLetter re: 1<213007, Trade/Device Name: Cerebra Sleep System . . . Received by Cerebra Medical Ltd., Jul. 6, 2022, 17 pages.

\* cited by examiner

US 12,329,497 B1

PROCESSING AND ANALYZING BIOMETRIC DATA

CROSS-REFERENCE TO RELATED APPLICATIONS

This application is a continuation of U.S. Non-Provisional patent application Ser. No. 18/299,539, filed Apr. 12, 2023, entitled "PROCESSING AND ANALYZING BIOMETRIC DATA," which is a continuation of U.S. patent application Ser. No. 17/833,894, filed Jun. 6, 2022, entitled "PROCESSING AND ANALYZING BIOMETRIC DATA," which claims priority to U.S. Provisional Patent Application No. 63/196,778, filed Jun. 4, 2021, entitled "PROCESSING AND ANALYZING BIOMETRIC DATA," each of which are incorporated herein by reference in their entireties.

GOVERNMENT LICENSE RIGHTS

This invention was made with government support under NSF Award ID 2136470 awarded by the National Science Foundation. The government has certain rights in the invention.

BACKGROUND

Sleep apnea, and other breathing disorders, are common among patients. Patients must undergo a variety of tests and be connected to a variety of sensors to detect the characteristics associated with these disorders. However, these systems are physically complex and lead to inaccurate and inadequate detection.

BRIEF DESCRIPTION OF THE DISCLOSURE

According to a first aspect, the present disclosure includes a cardiorespiratory analysis system comprising: a conformal patch comprising: an array of sensors comprising: a photoplethysmography (PPG) sensor; a 3-axis accelerometer; and an electrocardiogram (ECG) sensor; and a microcontroller wired to the PPG sensor, the 3-axis accelerometer, and the ECG sensor; and a compressible viscoelastic interface for attaching the microcontroller to at least one of the sensors of the array of sensors and to a patient; and a computing system comprising at least one processor and configured for: parsing sensor data received from the microcontroller into time series data associated with one or more data points of the sensor data, the one or more data points comprising: x axis data, y axis data, and z axis data derived from the 3-axis accelerometer; red data and IR data derived from the PPG sensor; and amplitude and frequency data derived from the ECG sensor; computing: a respiratory effort contraction during a first time window by: transforming the x axis data, y axis data, and/or z axis data into one or more amplitude envelopes; and identifying at least one trough of a particular decrement from a nearby baseline with a minimum width and distance of at least 10 seconds from any neighboring trough; a bradycardia event during a second time window by: calculating a heart rate based on the ECG or PPG data; and determining that the heart rate slowed by at least 6 beats per minute over a 6 second time period and at least 10 seconds distance from another nearby peak or trough; and a desaturation event during a third time window by: deriving a plurality of oxygen saturation (SpO2) data points over time based on the red data and IR data; and identifying at least one relative minimum in the SpO2 data points of a particular depth, a particular width, and a particular distance from other nearby SpO2 minima; and a tachycardia event during a fourth time window by: calculating a heart rate based on the ECG or PPG data; and determining that the heart rate increased by at least 6 beats per minute over a 6 second time period and at least 10 seconds distance from another nearby peak or trough; and an increase in respiratory effort during a fifth time window by: transforming the x axis data, y axis data, and/or z axis data into one or more amplitude envelopes; and identifying at least one peak of a particular height relatively to a nearby baseline with a minimum width and distance of at least 10 seconds from any neighboring peak; and an increase in pulse transit time (PTT) during a sixth time window by: determining that the PTT changed by at least 10 milliseconds over a 6 second time period and at least 10 seconds distance from another nearby peak or trough, wherein the PTT is a time between a first specified location on an ECG waveform and a second specified location on an PPG waveform; and determining that a respiratory disturbance occurred for the patient based upon the first time window, the second time window, the third time window, the fourth time window, the fifth time window and/or the sixth time window occurring in a particular order.

In a second aspect of the cardiorespiratory analysis system of the first aspect or any other aspect, wherein determining that the respiratory disturbance occurred for the patient is further based on determining that the first time window, the second time window, the third time window, the fourth time window, the fifth time window, and/or the sixth time window occurred within less than 45 seconds.

In a third aspect of the cardiorespiratory analysis system of the first aspect or any other aspect, wherein: the particular depth is 3%-4%; the particular width is 3 seconds; and the particular distance from the other nearby SpO2 minima is 10 seconds.

In a fourth aspect of the cardiorespiratory analysis system of the first aspect or any other aspect, wherein the computing system is further configured for determining a first dyad by determining that the desaturation event occurred within a second predetermined time after the respiratory effort contraction.

In a fifth aspect of the cardiorespiratory analysis system of the fourth aspect or any other aspect, wherein the computing system is further configured for determining a second dyad by determining that the tachycardia event occurred within a third predetermined time after the respiratory effort contraction.

In a sixth aspect of the cardiorespiratory analysis system of the fifth aspect or any other aspect, wherein the computing system is further configured for determining that the first dyad and the second dyad occurred in temporal order.

In a seventh aspect of the cardiorespiratory analysis system of the first aspect or any other aspect, wherein: deriving the plurality of SpO2 data points over time based on the red data and the IR data comprises determining a plurality of optical ratios by: splitting the red data into a red AC signal and a red DC signal; splitting the IR data into an IR AC signal and an IR DC signal; and computing:

$$R = \frac{AC_{rms\ RED} / DC_{rms\ RED}}{AC_{rms\ IR} / AC_{rms\ IR}}$$

wherein: R is an optical ratio; $AC_{rms\ RED}$ is a root means square of the red AC data; $DC_{rms}$ RED is a root means square of the red DC data; $AC_{rms}$ IR is a root means square of the IR AC data; and $DC_{rms}$ IR is a root means square of the IR DC data.

In an eighth aspect of the cardiorespiratory analysis system of the seventh aspect or any other aspect, wherein the computing system is further configured for removing baseline wander from the red DC signal and the IR DC signal by removing a particular range of values from the red DC signal and the IR DC signal based on a number of baseline data shifts included in the ECG data.

In a ninth aspect of the cardiorespiratory analysis system of the eighth aspect or any other aspect, wherein the computing system is configured for: determining a plurality of PPG beats based on the red AC signal and the IR AC signal; computing a template comprising averaging a portion of the plurality of PPG beats over time; comparing the template to each PPG beat; and discarding one or more PPG beats of the plurality of PPG beats that do not match the template.

In a tenth aspect of the cardiorespiratory analysis system of the first aspect or any other aspect, wherein one or more of the first time window, the second time window, the third time window, the fourth time window, the fifth time window, and the sixth time window occur simultaneously.

In an eleventh aspect of the cardiorespiratory analysis system of the first aspect or any other aspect, wherein the particular order is temporal order.

According to a twelfth aspect, the present disclosure includes a process for computing respiratory disturbances comprising: parsing, via at least one processor, sensor data received from a microcontroller of a conformal patch into time series data associated with one or more data points of the sensor data, the one or more data points comprising: x axis data, y axis data, and z axis data derived from a 3-axis accelerometer; red data and IR data derived from a photoplethysmography (PPG) sensor; and amplitude and frequency data derived from an electrocardiogram (ECG) sensor; computing via the at least one processor: a respiratory effort contraction during a first time window by: transforming the x axis data, y axis data, and/or z axis data into one or more amplitude envelopes; and identifying at least one trough of a particular decrement from a nearby baseline with a minimum width and distance of at least 10 seconds from any neighboring trough; a bradycardia event during a second time window by: calculating a heart rate based on the ECG or PPG data; and determining that the heart rate slowed by at least 6 beats per minute over a 6 second time period and at least 10 seconds distance from another nearby peak or trough; and a desaturation event during a third time window by: deriving a plurality of oxygen saturation (SpO2) data points over time based on the red data and IR data; and identifying at least one relative minimum in the SpO2 data points of a particular depth, a particular width, and a particular distance from other nearby SpO2 minima; and a tachycardia event during a fourth time window by: calculating a heart rate based on the ECG or PPG data; and determining that the heart rate increased by at least 6 beats per minute over a 6 second time period and at least 10 seconds distance from another nearby peak or trough; and an increase in respiratory effort during a fifth time window by: transforming the x axis data, y axis data, and/or z axis data into one or more amplitude envelopes; and identifying at least one peak of a particular height relatively to a nearby baseline with a minimum width and distance of at least 10 seconds from any neighboring peak; and an increase in pulse transit time (PTT) during a sixth time window by: determining that the PTT changed by at least 10 milliseconds over a 6 second time period and at least 10 seconds distance from another nearby peak or trough, wherein the PTT is a time between a first specified location on an ECG waveform and a second specified location on an PPG waveform; and determining that a respiratory disturbance occurred for a patient based upon the first time window, the second time window, the third time window, the fourth time window, the fifth time window and/or the sixth time window occurring in a particular order.

In a thirteenth aspect of the process for computing respiratory disturbances of the twelfth aspect or any other aspect, wherein determining that the respiratory disturbance occurred for the patient is further based on determining that the first time window, the second time window, the third time window, the fourth time window, the fifth time window, and/or the sixth time window occurred within less than 45 seconds.

In a fourteenth aspect of the process for computing respiratory disturbances of the twelfth aspect or any other aspect, wherein: the particular depth is 3%-4%; the particular width is 3 seconds; and the particular distance from the other nearby SpO2 minima is 10 seconds.

In a fifteenth aspect of the cardiorespiratory analysis system of the twelfth aspect or any other aspect, wherein the computing system is further configured for determining a first dyad by determining that the desaturation event occurred within a second predetermined time after the respiratory effort contraction.

In a sixteenth aspect of the cardiorespiratory analysis system of the fifteenth aspect or any other aspect, wherein the computing system is further configured for determining a second dyad by determining that the tachycardia event occurred within a third predetermined time after the respiratory effort contraction.

In a seventeenth aspect of the cardiorespiratory analysis system of the sixteenth aspect or any other aspect, wherein the computing system is further configured for determining that the first dyad and the second dyad occurred in temporal order.

In an eighteenth aspect of the cardiorespiratory analysis system of the twelfth aspect or any other aspect, wherein: deriving the plurality of SpO2 data points over time based on the red data and the IR data comprises determining a plurality of optical ratios by: splitting the red data into a red AC signal and a red DC signal; splitting the IR data into an IR AC signal and an IR DC signal; and computing:

$$R = \frac{AC_{rms\,RED} / DC_{rms\,RED}}{AC_{rms\,IR} / AC_{rms\,IR}}$$

wherein: R is an optical ratio; $AC_{rms}$ RED is a root means square of the red AC data; $DC_{rms}$ RED is a root means square of the red DC data; $AC_{rms}$ IR is a root means square of the IR AC data; and $DC_{rms}$ IR is a root means square of the IR DC data.

In a nineteenth aspect of the cardiorespiratory analysis system of the eighteenth aspect or any other aspect, wherein the computing system is further configured for removing baseline wander from the red DC signal and the IR DC signal by removing a particular range of values from the red DC signal and the IR DC signal based on a number of baseline data shifts included in the ECG data.

In a twentieth aspect of the cardiorespiratory analysis system of the nineteenth aspect or any other aspect, wherein the computing system is configured for: determining a plurality of PPG beats based on the red AC signal and the IR AC signal; computing a template comprising averaging a portion of the plurality of PPG beats over time; comparing the template to each PPG beat; and discarding one or more PPG beats of the plurality of PPG beats that do not match the template.

In a twenty-first aspect of the cardiorespiratory analysis system of the twelfth aspect or any other aspect, wherein one or more of the first time window, the second time window, the third time window, the fourth time window, the fifth time window, and the sixth time window occur simultaneously.

In a twenty-second aspect of the cardiorespiratory analysis system of the twelfth aspect or any other aspect, wherein the particular order is temporal order.

In a twenty-third aspect of the cardiorespiratory analysis system of the twelfth aspect or any other aspect, wherein quality and fidelity of the calculated SpO2 are indexed by computing a normalized cross-correlation or Pearson's correlation coefficient between pulsatile red and IR signals within a time window of up to 10 seconds in length.

In a twenty-fourth aspect of the cardiorespiratory analysis system of the twelfth aspect or any other aspect, wherein the determination of a respiratory disturbance is gated by sleep stage as determined by a combination of information regarding motion and cardiovascular state.

In a twenty-fifth aspect of the cardiorespiratory analysis system of the twenty-fourth aspect or any other aspect, wherein the information regarding motion comprises amplitude- and spectral-based features of actigraphy computed in windows of length 30 seconds or greater.

In a twenty-sixth aspect of the cardiorespiratory analysis system of the twenty-fourth aspect or any other aspect, wherein the information regarding cardiovascular state comprises time- and frequency-domain features of heart rate computed in windows of length 30 seconds or greater.

In a twenty-seventh aspect of the cardiorespiratory analysis system of the twenty-fourth aspect or any other aspect, wherein these windowed features are used as inputs to a supervised machine learning model which renders time-varying sleep stage estimations in windows of length 30 seconds or greater.

According to a twenty-eighth aspect, the present disclosure includes a method for treating sleep disorders comprising: determining that a patient has experienced a respiratory disturbance by computing: a respiratory contraction during a first time window by: transforming x axis data, y axis data, and/or z axis data received from a 3-axis accelerometer into one or more amplitude envelopes; and identifying at least two troughs of the one or more amplitude envelopes separated by at least 10 seconds; a desaturation event during a second time window by: deriving a plurality of oxygen saturation (SpO2) data points over time based on red data and IR data received from a photoplethysmography (PPG) sensor; and identifying at least one SpO2 data point below a certain threshold; and a tachycardia event during a third time window by: calculating a heart rate based on electrocardiogram (ECG) data received from an ECG sensor; and determining that the heart rate slowed to one beat per 8-10 seconds; determining that the first time window, the second time window, and the third time window occurring in temporal order; upon determining that the patient has experienced the respiratory disturbance, administering treatment to reduce future respiratory disturbances for the patient.

In a twenty-ninth aspect of the method for treating sleep disorders of the twenty-eighth aspect or any other aspect, further comprising receiving an order for a patch device comprising the 3-axis accelerometer, the PPG sensor, and the ECG sensor.

In a thirtieth aspect of the method for treating sleep disorders of the twenty-ninth aspect or any other aspect, further comprising facilitating shipping the patch device to the patient.

In a thirty-first aspect of the method for treating sleep disorders of the thirtieth aspect or any other aspect, further comprising receiving the patch device from the patient.

In a thirty-second aspect of the method for treating sleep disorders of the thirty-first aspect or any other aspect, further comprising downloading the x axis data, the y axis data, the z axis data, the red data, the IR data, and the ECG data from the patch device.

In a thirty-third aspect of the method for treating sleep disorders of the thirty-second aspect or any other aspect, wherein a portion of the patch device is disposable.

In a thirty-fourth aspect of the method for treating sleep disorders of the thirty-second aspect or any other aspect, wherein administering treatment to reduce future respiratory disturbances for the patient comprises recommending an airway pressure device.

In a thirty-fifth aspect of the method for treating sleep disorders of the thirty-second aspect or any other aspect, wherein administering treatment to reduce future respiratory disturbances for the patient comprises recommending oral appliances, oxygen, or other devices.

The third-party systems and processes overcome many of the shortcomings and limitations of prior systems for detecting and analyzing biometric data.

Third-party systems fail to provide the ability to observe and monitor a variety of patient data points. Additionally, they fail to provide a single device attached at one location on a patient to observe each of these data points. The present disclosure provides for a single patch for monitoring and retrieving a plurality of data points from a patient. Additionally, the present disclosure provides a method and system for calculating and evaluating those various biometric data points while also detecting disorders of a patient associated with such data.

Using the method and system as disclosed, a provider may be able to easily identify issues associated with a patient and provide a diagnosis. Sleep apnea, and other breathing disorders, are common among patients, and through the use of the methods and systems of the present disclosure, these disorders can be more easily and with more accuracy be diagnosed and treated.

Figure 1:
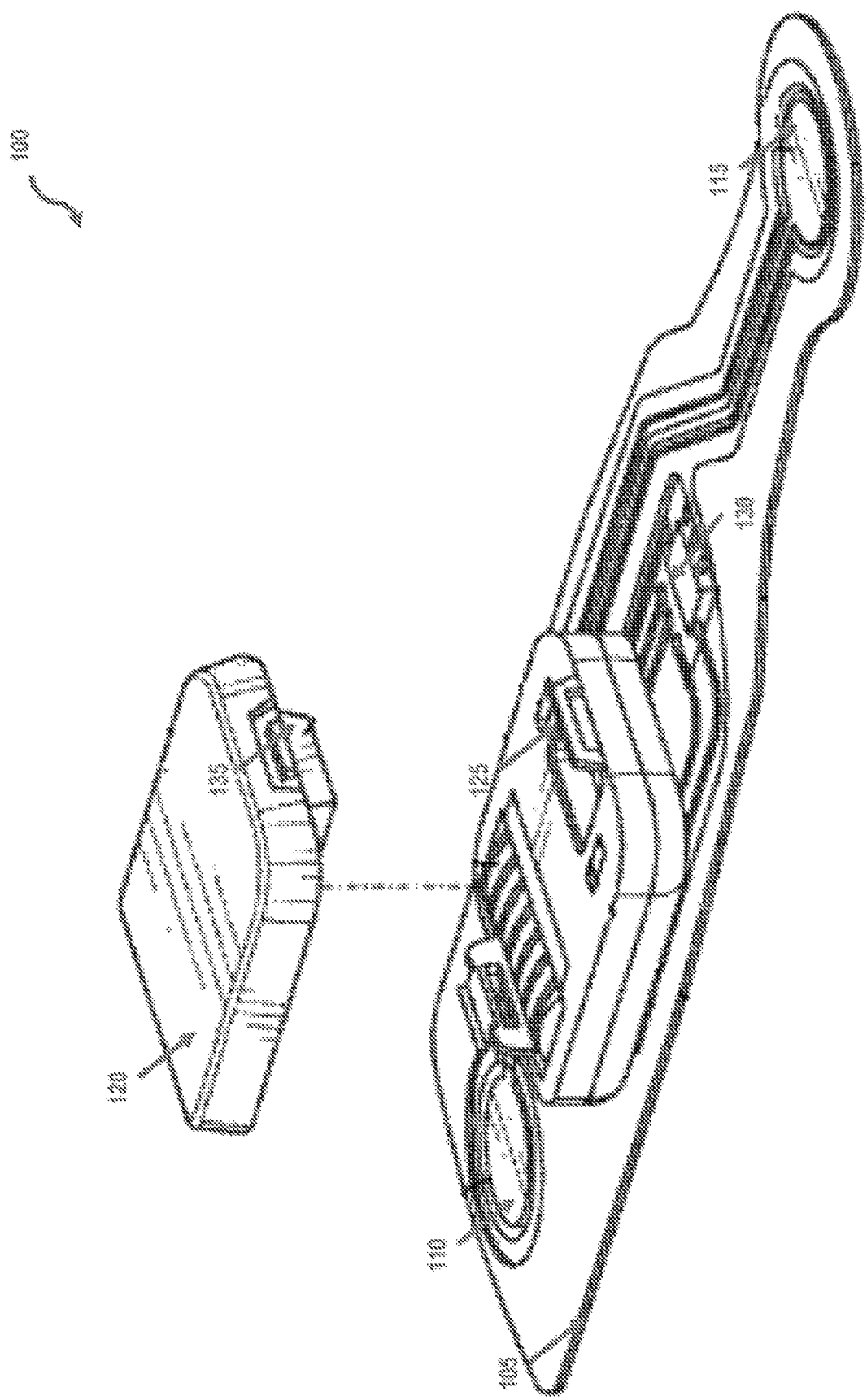
FIG. 1 illustrates a top perspective view of an example patch device 100 according to various embodiments of the present disclosure.

While the disclosure is susceptible to various modifications and alternative forms, a specific embodiment thereof is shown by way of example in the drawings and will herein be described in detail. It should be understood, however, that the drawings and detailed description presented herein are not intended to limit the disclosure to the particular embodiment disclosed, but to the contrary, the intention is to cover all modifications, equivalents, and alternatives falling within the spirit and scope of the present disclosure as defined by the appended claims.

DETAILED DESCRIPTION

This disclosure will now be described with reference to the drawing figures, in which like reference numerals refer to like parts throughout. For purposes of clarity in illustrating the characteristics of the present disclosure, proportional relationships of the elements have not necessarily been maintained in the drawing figures.

FIG. 1 illustrates a top perspective view of an example patch device 100 according to various embodiments of the present disclosure. In some embodiments, the patch device 100 is similar to that the patch device described in detail in commonly assigned U.S. patent application Ser. No. 17/199,181 titled "PATCH FOR IMPROVED BIOMETRIC DATA CAPTURE AND RELATED PROCESSES" filed on Mar. 11, 2021, which is incorporated herein by reference. Relevant to the present disclosure, the patch device 100 can include a flexible circuit layer 105, which may include a bottom adhesive layer, a receptacle cover 120, a battery receptacle 125, and a plurality of sensors. In one embodiment, the bottom adhesive layer of the flexible circuit layer 105, the receptacle cover 120, or the battery receptacle 125 includes a microcontroller that executes the applications as discussed herein and is in communication with the sensors.

The sensors may be used to collect data points. According to at least one embodiment, the sensors collect data from the patch device 100 attached to a patient. The sensors may be wired to the computing system (which will be discussed with reference to FIG. 2 below) or may be wireless. In some embodiments, the sensors may include a first electrocardiogram (ECG) electrode 110, a second ECG electrode 115, a photoplethysmography (PPG) sensor layer 130, and/or an accelerometer 135. The PPG sensor layer 130 may include a PPG sensor. Certain sensors (e.g., PPG, ECG) may produce better (e.g., higher amplitude) or more consistent signals when adhered or pressed against the chest of the patient (even when a chest expands/contracts and/or when a patient rolls during sleep). In various embodiments, it may be advantageous for one or more of these sensors to be coupled to a flexible and/or stretchable substrate (e.g., the flexible circuit layer 105) and otherwise be isolated from rigid components (e.g., a circuit board).

In some embodiments, the sensors include an ECG sensor made up of the first ECG electrode 110 and/or the second ECG electrode 115. In some embodiments, the ECG sensor includes an ECG electrode and a ground.

The ECG electrodes 110 and 115 may have a circular shape with a certain diameter, such as, but not limited to, 15 to 25 millimeters. According to at least one embodiment, the ECG electrodes 110 and 115 may be directly in contact with the patient's skin. When in direct contact, there are no additional layers between the patient's skin and the ECG electrodes 110 and 115. In some embodiments, the ECG sensor is not directly in contact with a patient's skin. In these embodiments (and others), there is a layer of hydrogel (or other suitable material) between the ECG sensor and the patient's skin.

In various embodiments, the ECG sensor is configured to be used by the microcontroller to measure the electrocardiogram on the patch device 100, which can be further used to determine cardiorespiratory parameters. The ECG sensor can read, monitor, and measure electrical activity (e.g., voltage) of a patient's heart over time (among other things). The ECG sensor may detect a heartbeat or other electrical properties of the heart via the voltage changes in the user's heart. The ECG sensor may also include an ECG amplifier. In some embodiments, the ECG sensor can include a two-lead, a three-lead, or other number of lead ECG sensor. The ECG sensor can also include a heart rate sensor and a pulse oximeter.

In one embodiment, the sensors include the PPG sensor in the PPG sensor layer 130. In some embodiments, the PPG sensor interprets data from red/infrared (IR) light. In various embodiments, the PPG sensor is configured to measure at least the patient's pulse rate and pulse rate variability, respiratory rate, and blood flow. The PPG sensor may measure volumetric variations of blood circulation at the surface of the user's skin via optics. The PPG sensor may perform reflectance-mode photoplethysmorgram signal detection of a design and sampling range of 50-200 Hz. In some embodiments, the PPG sensor may be configured to monitor, measure, and/or sense sensor measurements, such as, but not limited to, vasoconstriction, heart rate, SpO2 levels, cutaneous blood flow and volume, which will be discussed further in reference to FIG. 5.

According to at least one embodiment, the PPG sensor can include an array board with a plurality of light emitting diodes (LEDs) and a plurality of photodiodes (PDs). The array board may include alternating individual LEDs and PDs on the array board such that each individual LED is proximate to individual PDs, and each individual PD is proximate to individual LEDs. For example, the array board can include a printed circuit board (PCB) with pairs of apertures for leads of a PD or an LED spaced a part at a specific distance. The specific distance may be greater than or equal to 6 mm, 6 mm, 9 mm, 12 mm, or some other distance as can be appreciated.

In various embodiments, the patch device 100 may include an adaptive filter configured to reduce a noise of readings from the plurality of PDs or other components of the patch device 100. The adaptive filter can be applied to a measurement or signal from the PPG sensor and/or the ECG sensor to extract information using frequency-domain or time-domain features. As an example, the adaptive filter can extract beat-to-beat heartbeats from a data signal corresponding to the PPG sensor and/or the ECG sensor.

In one embodiment, the accelerometer 135 is a three-axis accelerometer, which may be wired to the microcontroller. The microcontroller can derive x-axis data, y-axis data, and z-axis data from the three-axis accelerometer and send the data for further processing. As will be understood from discussions herein, in various embodiments, the data corresponds to various measurements of the patient's sleeping position or body orientation. This data may be observed to determine which way the patient is sleeping, which can be useful for determining effects of how the patient sleeps on the patient's respiratory patterns.

In one embodiment, the data is in a binary format when received by the microcontroller. The microcontroller is configured to derive the data using a processing script.

According to at least one embodiment, the patch device 100 can provide a singular continuous area of contact to collect various sensor measurements. This continuous area of contact can limit the impact of inevitable patient movement on the collection of data. Moreover, the continuous area of contact can prevent inaccurate or inconsistent data from being collected from the patient.

Figure 2:
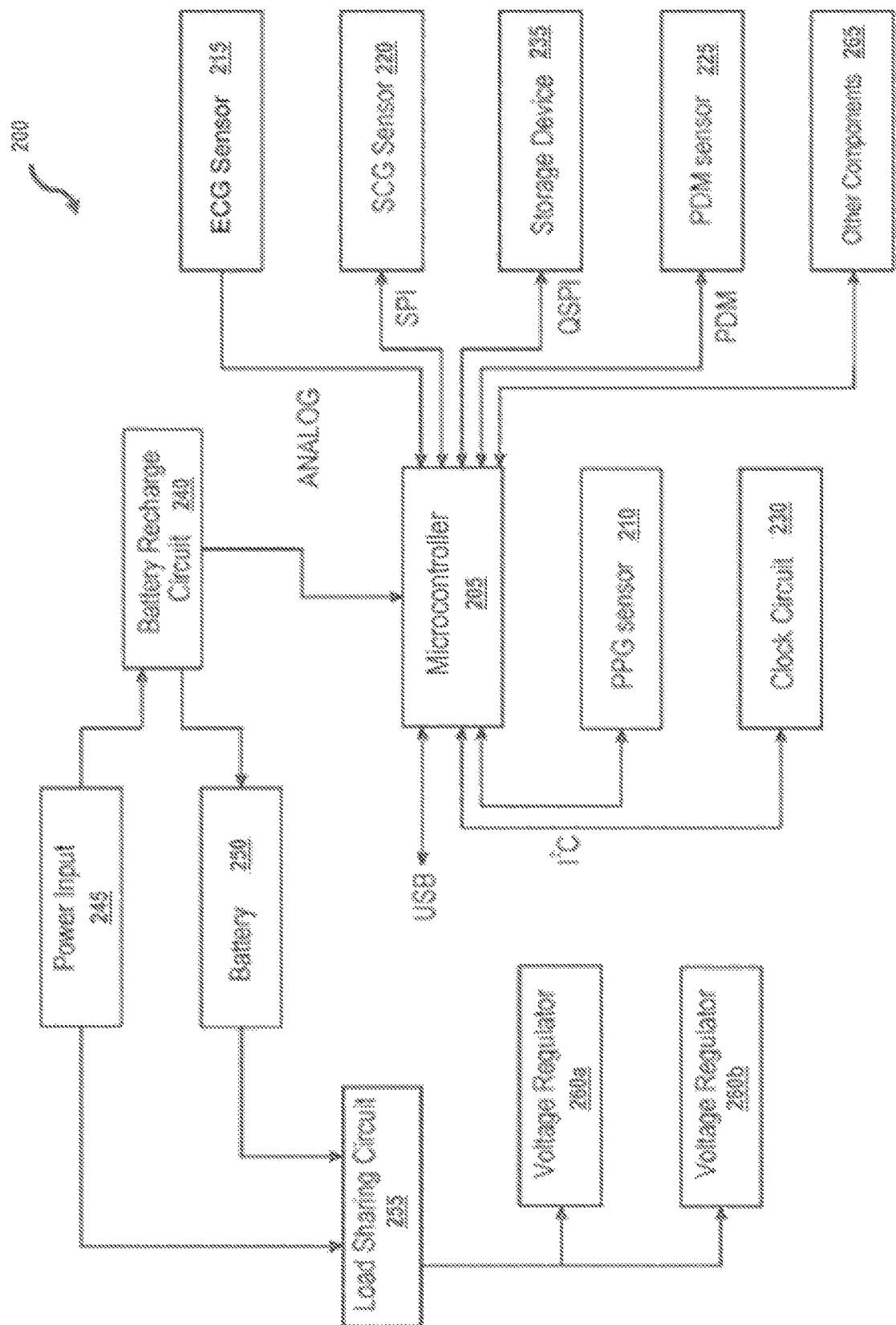
FIG. 2 illustrates a functional circuit diagram for the patch device 100 (as shown in FIG. 1) according to various embodiments of the present disclosure.

FIG. 2 illustrates a functional circuit diagram for the patch device 100 (as shown in FIG. 1) according to various embodiments of the present disclosure and similar to that as described in detail in commonly assigned U.S. patent application Ser. No. 17/199,181 titled "PATCH FOR IMPROVED BIOMETRIC DATA CAPTURE AND RELATED PROCESSES" filed on Mar. 11, 2021, which is incorporated herein by reference. The circuit diagram 200 can include a microcontroller 205 in communication with one or more sensors shown as PPG sensor 210, ECG sensor 215, SCG sensor 220, and PDM sensor 225, among other sensors. The microcontroller 205 can be in communication with a clock circuit 230, a storage device 235, and a battery recharge circuit 240.

In various embodiments, the battery recharge circuit 240 can receive power from a power input 245 and use the received power to charge the battery 250. The power input 245 can be coupled to an external power signal and the battery recharge circuit 240 can store power from the external power signal in the battery 250. The load sharing circuit 255 can provide power from the battery 250 when the battery recharge circuit 240 is not receiving the external power signal and provide the input power signal from the power input 245 when the battery recharge circuit 240 is receiving the external power signal. Stated differently, the load sharing circuit 255 can receive power from either the power input 245, the battery 250, or the power input 245 and the battery 250.

The load sharing circuit 255 can provide a power signal to one or more voltage regulators, such as voltage regulators 260a and 260b. In one embodiment, the voltage regulator 260a can provide a first input voltage to one or more circuit components, and the voltage regulator 260b can provide a second input voltage to one or more other circuit components.

The circuit diagram 200 can include other components 265, which may or may not be coupled directly to the microcontroller 205. The other components 265 can include one or more radio frequency filters coupled to the microcontroller 205 and one or more antennas coupled to the radio frequency filter. In one embodiment, the other components 265 include a gyroscope. In one embodiment, the other components 265 include an accelerometer. In one embodiment, the other components 265 include a compass. In one embodiment, the other components 265 include a digital motion processor, which can be configured to offload computation of motion processing algorithms from the microcontroller 205.

Figure 3:
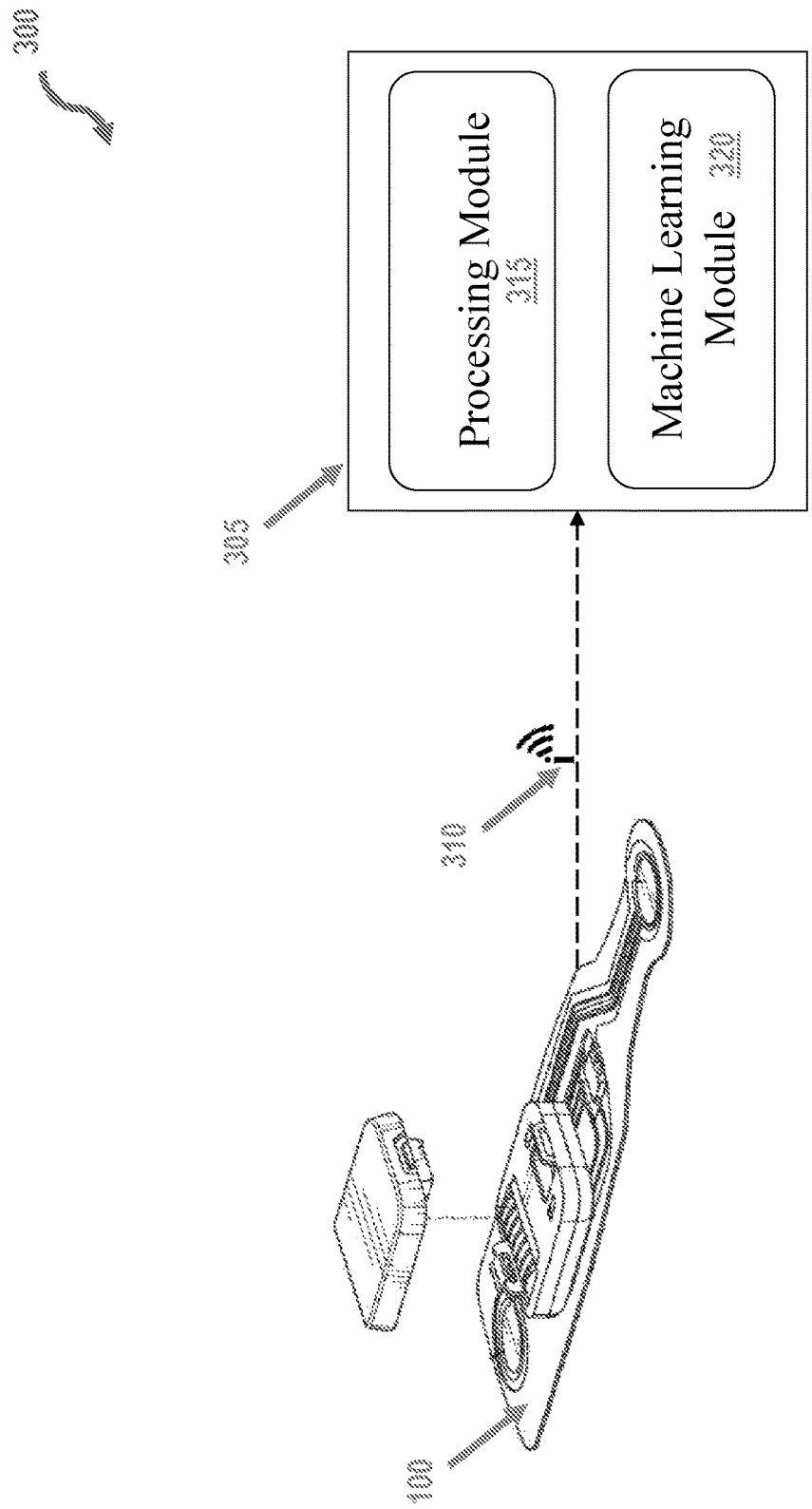
FIG. 3 is a computing architecture diagram illustrating the connection between a patch device and a computing system according to various embodiments of the present disclosure.

FIG. 3 is a computing architecture diagram illustrating the connection between a patch device and a computing system according to various embodiments of the present disclosure. In one embodiment, the patch device is the patch device 100 from FIG. 1.

According to at least one embodiment, the patch device 100 is connected to the computing system 305 via an internet connection 310. In one embodiment, the internet connection 310 allows the data collected from the patch device to be processed and analyzed at the computing system 305.

In one or more embodiments, the patch device is connected to the computing system 305 via another suitable mechanism. For example, after use by a patient, the patch device 100 might be connected to the computing system 305 and data downloaded to the computing system 305 from the patch device 100. Continuing with this example, the patch device 100 might be connected to the computing system 305 via another suitable mechanism, including, but not limited to, a wired connection (e.g., a port connected to the microcontroller, which may be the microcontroller 205 from FIG. 2), a near-field communications connection, a Bluetooth connection, cellular, or a contact connection (e.g., via one or more contacts for data transfer on the patch device 100).

The computing system 305 has a processing module 315 and a machine learning module 320. In one embodiment, the processing module 315 is configured to parse the data collected by the patch device 100 and determine if an issue (e.g., breathing irregularity, sleep position strain, cardiac issues, and respiratory issues) exists based on the parsed data. The data that can be parsed by the processing module will be discussed herein with reference to FIGS. 4 and 5. According to at least one embodiment, the processing module 315 can complete initial processing of various data points. Additionally, the processing module 315 may complete autoscoring, which will be discussed further with reference to FIG. 7.

In one embodiment, the machine learning module 320 is configured to receive the data collected by the patch device 100 and an apnea-hypopnea index (AHI) for the patient whose data was received. The data collected may be raw data in a binary format. In one embodiment, the machine learning module 320 is configured to calculate various features as discussed with reference to FIG. 5. According to at least one embodiment, the machine learning module 320 receives a variety of inputs, trains one or more machine learning models based on known outputs, and predicts diagnoses for the patient based on the correlation between the inputs and known outputs.

As will be understood from discussions herein, the system may receive raw data from the one or more sensors of the patch device 100. The system may then parse the raw data, derive features from the data, and then use the raw data and/or derived features to estimate, compute, or determine one or more characteristics of a patient (e.g., a likelihood of sleep apnea, a AHI score, etc.), each of which will be discussed below.

Figure 4:
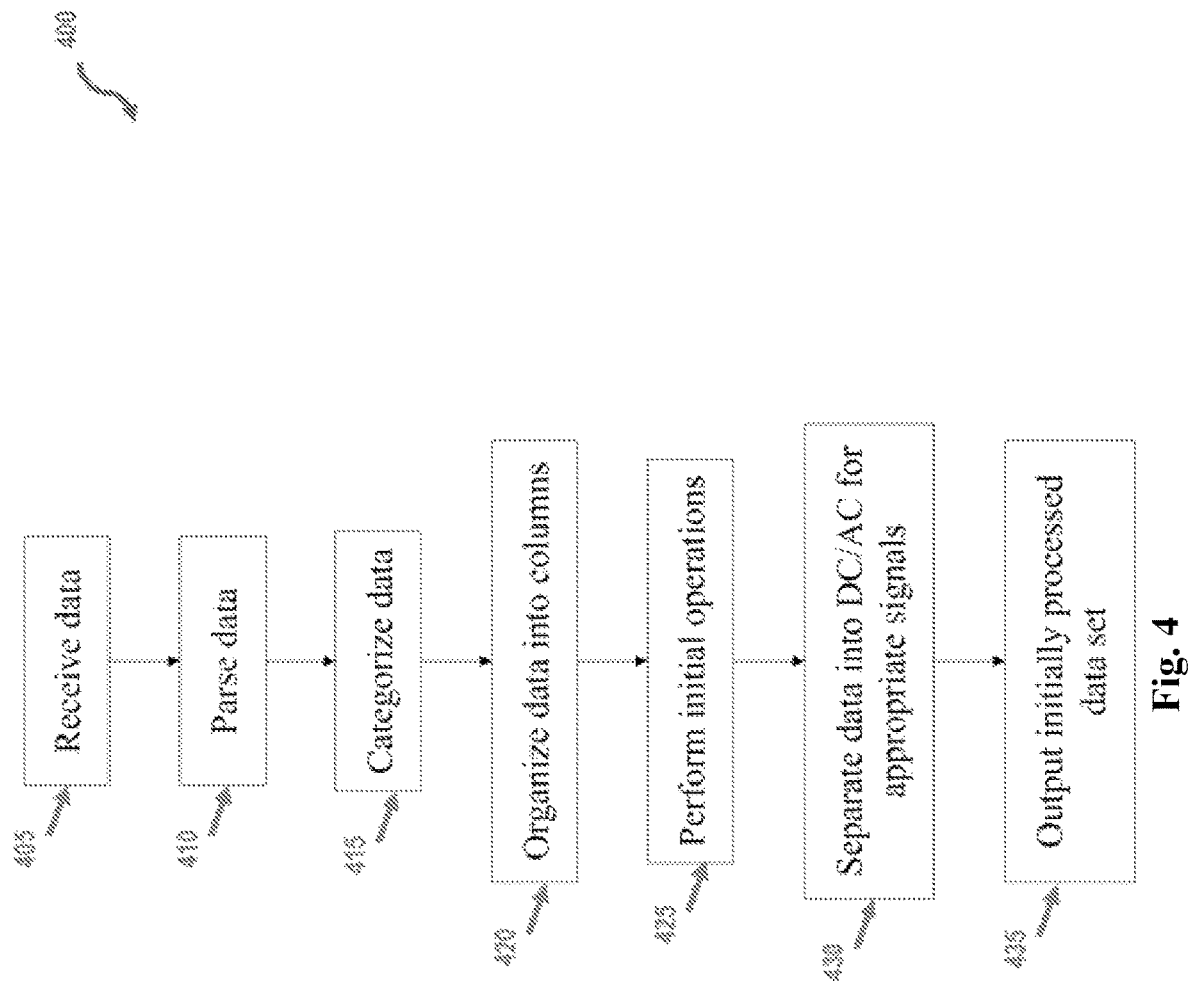
FIG. 4 is a flowchart describing a process for determining one or more signal-derived features/metrics according to various embodiments of the present disclosure.

FIG. 4 is a flowchart describing a process for determining one or more signal-derived features/metrics according to various embodiments of the present disclosure. In various embodiments, and as will be further discussed herein, data is received by the system, which then is transformed into a parameter with a timeseries (e.g., a series of data points that are indexed in time order).

The flowchart begins at block 405, where data is received. In one embodiment, the received data is the data from the patch device 100 used by the patient. In one embodiment, the system can extract the timeseries from a raw data file (e.g., received from the patch device 100). In various embodiments, the data is received from the plurality of sensors and may be in binary format. In one embodiment, the data from each sensor is received as its own binary file. One advantage to a central microcontroller being used, as illustrated in FIG. 2, is that all of the data is being received at one central microcontroller. This allows for all of the data to be received at one location and associated with the same set of time data (e.g., from the clock or a like component). Further, using a single microcontroller may eliminate programming and hardware complexities as the single microcontroller and collect and collate all sensor data into a single or multiple data files.

At block 410, the system parses the received data. In at least one embodiment, the system parses the received data into individual sensor data (e.g., if the sensor data is bulk data with data from multiple sensors in a single data file), into data based on time information (e.g., segments data into discrete time segments), and/or parses the received data into discrete information, such as, for example, separate red and IR data received from the PPG sensor.

At block 415, the system categorizes the data. In one or more embodiments, the system categorizes the data into different data types (e.g., PPG data, etc.) and/or column vectors discussed below in relation to block 420. In some embodiments, the system categorizes the data into DC and AC data (discussed below). In at least one embodiment, the system categorizes the data into noisy and clean data based on a preliminary analysis of the received data.

At block 420, the system organizes the data into a plurality of columns corresponding to the categories as determined at block 415. In one embodiment, the timeseries is stored in column vectors, which may correspond to: timestamps, three-axis accelerometer, IR, PPG, and ECG.

At block 425, initial operations are performed. In one embodiment, the system can precondition each timeseries to remove filler values, (e.g., values of −1 from the lower data rate PPG) and can resample the timeseries using the method of interpolation. Interpolation can include a process of upsampling a set of data and filtering the upsampled data. According to at least one embodiment, the system determines one or more Nyquist frequency for one or more signals. The system can use interpolation to generate timeseries to have sampling rates above twice the Nyquist frequency of the given signal. As an example, the system can utilize a sampling rate greater than twice the Nyquist frequency. The system can prevent aliasing by using a sampling rate above twice the Nyquist frequency. The system can down sample the interpolated timeseries to reduce file size. The system can reduce an algorithm runtime by down sampling the interpolated timeseries. According to one embodiment, the following values are the constant sampling rates for resampling particular signals of respective sensors: Raw accelerometer @ 500 Hz (for seismocardiogram (SCG), phonocardiogram (PCG)), ECG @ 250 Hz, and PPG @ 50 Hz.

At block 430, the data is separated as either a pulsatile component (AC) or non-pulsatile component (DC), whichever may be appropriate. In various embodiments, the system separates data collected from various sensors (e.g., ECG, PPG, and accelerometer, etc.) into AC and DC components. In at least one embodiment, the DC component is a set of values that may contain a baseline wander and the AC component is a set of values that may exclude the baseline wander. In particular embodiments, baseline wander is a type of noise produced in various sensors, though primarily in an ECG sensor.

At block 435, the system outputs (or saves to memory) the initially processed data for further use, which will be discussed with reference to figures below.

Figure 5:
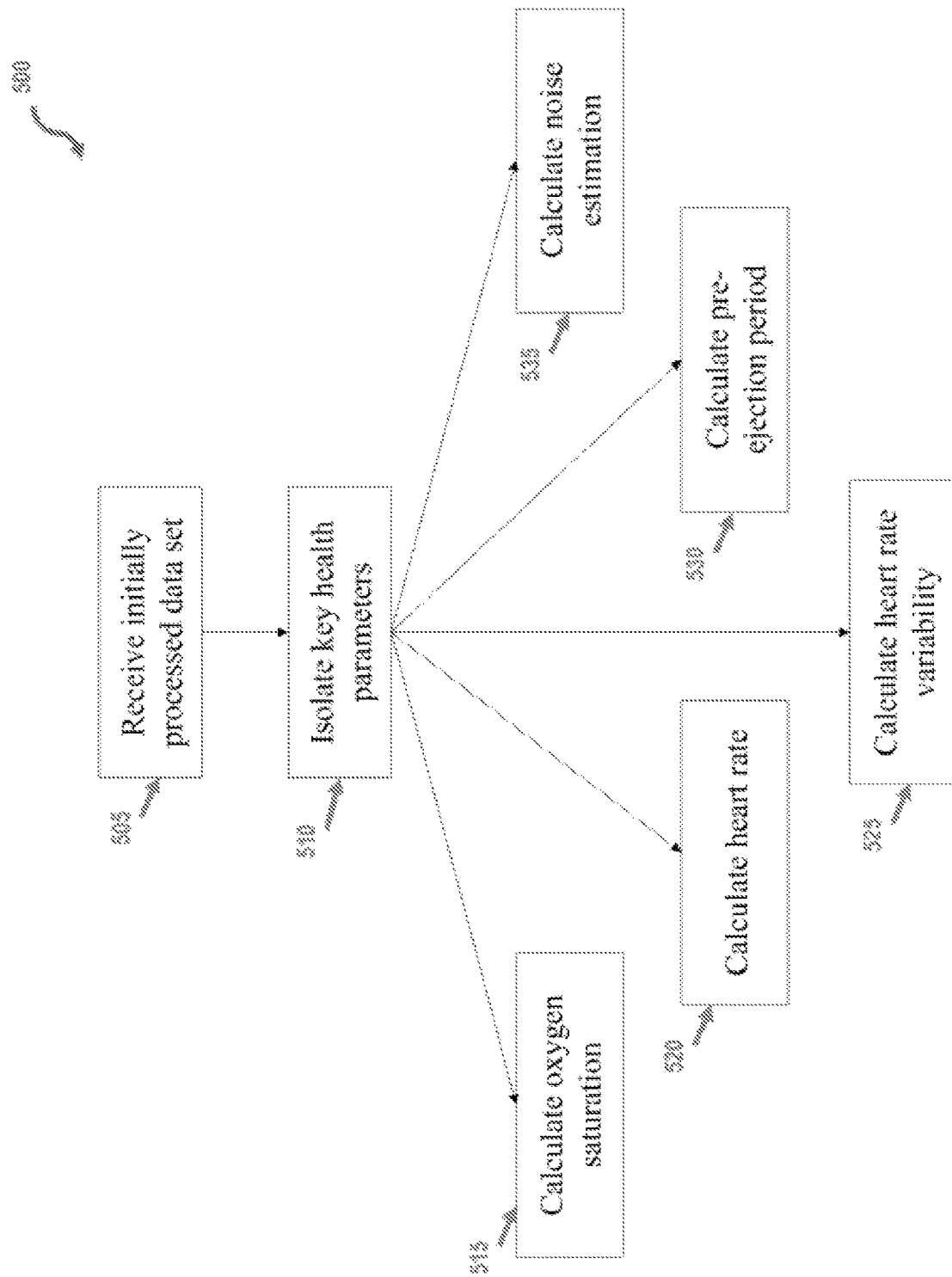
FIG. 5 is a flowchart illustrating the calculation of a variety of derived parameters according to various embodiments of the present disclosure.

FIG. 5 is a flowchart illustrating computation of a variety of derived parameters according to various embodiments of the present disclosure. Many parameters may be derived, including, but not limited to, oxygen saturation (SpO2), heart rate (HR), HRV, pre-ejection period (PEP), and noise estimation from the data collected by the sensors, including the PPG sensor (as discussed with reference to FIG. 1).

At block 505, the initially processed data set is received. In one embodiment, the initially processed data set corresponds to those processed and outputted at block 435 in FIG. 4.

At block 510, key health parameters are isolated. In one embodiment, the system can apply filters to the data to extract or isolate key health parameters. As an example, the system can apply a bandpass filter to a data signal to isolate a specific band of frequency for further processing. As an example, the system can digitally bandpass filter the AC content of both the red and IR PPG channels at a range usually around 0.5-6 Hz. The system can segment the filtered PPG data according to the R-peaks for subsequent analysis. The system can take the ratio of the AC signal with respect to the DC signal of each PPG channel. Taking this ratio can be referred to as taking the perfusion index. The flowchart then proceeds to at least one of blocks 515, 520, 525, 530, 535, and/or 540.

At block 515, the oxygen saturation content is calculated. In one embodiment, the system can calculate the SpO2 content in a variety of ways by using the processed PPG's AC and DC data. The system can employ the optical ratio (R) to 25 calculate the SpO2 content. The optical ratio can be a ratio of ratios between the Red's AC and DC data and the IR's AC and DC data.

In one example, the following formula can illustrate an exemplary optical ratio:

$$R = \frac{AC_{rms\,RED} / DC_{rms\,RED}}{AC_{rms\,IR} / AC_{rms\,IR}}$$

Where the R can represent the optical ratio, $AC_{rms}$ RED can represent the root means square of AC data collected by red lights in the PPG, $DC_{rms}$ RED can represent the root means square of DC data collected by red lights in the PPG, $AC_{rms}$ IR can represent the root means square of AC data collected by IR lights in the PPG, and $DC_{rms}$ IR can represent the root means square of DC data collected by IR lights in the PPG. In some embodiments, other formulas for optical ratio may be utilized. The other formulas may be selected based on a lower error rate when compared to the above-referenced formula. The above-formula is included herein for exemplary purposes.

In one embodiment, the system can calculate the optical ratio by using one or more of the following methods. The least-square-optimized (LSQ) method can be used by calculate a value of R by minimizing the error shown in the following formula:

$$e = AC_{RED} - R * AC_{IR}$$

Where e can represent the error, $AC_{RED}$ can represent the AC data collected by the red light in the PPG, and $AC_{IR}$ can represent the data collected by the IR light in the PPG. Other methods the system can use to calculate the optical ratio include beat-to-beat (B2B), exponentially weighted moving average (EWMA), beat-averaged (AVG), intervallic (INT), intervallic FFT, intervallic peak (PKS), and enveloped (ENV), etc. In some embodiments, the system can compute the optical ratio using multiple methods to verify, average, identify problems, or otherwise improve the optical ratio determination. The system can use a B2B method for calculating the optical ratio by taking the peak-to-peak amplitude ratios of the DC and pulsatile (AC) data, collected from the segmented PPG beat. The system can use a EWMA method for calculating the optical ratio by taking the B2B data and smoothening it with a weighted moving average filter and a forgetting factor of A (lambda)>0.75. The "forgetting factor" can refer to a value which gives exponentially less weight to older error samples. The system can use AVG as a method to calculate the optical ratio by using the same methodology as B2B, but applying that methodology to interval-averaged PPG beats (e.g., the ensemble average of all PPG beats with a certain time window). The system can use INT as a method to calculate the optical ratio by defining the AC and DC values across a given time window segment of the PPG data (instead of beat-to-beat). The system can apply an FFT to segmented time intervals of the raw PPG signal, and each segment's spectrum can be used to define the AC and DC content of the PPG channel, with the AC amplitude corresponding to the maximum peak in the cardiac frequency band (e.g., between 0.5 and 2.5 Hz). The system can use PKS as a method for calculating the optical ratio by detecting peaks from red and IR pulses in a given window and calculating the ratios of the peaks from red and IR pulses. These ratios can be average for a given time interval. The system can use ENV as a method for calculating the optical ratio by defining the pulsatile (AC) amplitude for a given interval. This AC value can be calculated using an envelope constructed by a rolling window maximum operation. Envelopes in this context may be used as a method for calculating the optical ratio by defining the pulsatile amplitude for a given interval.

At block 520, heart rate is calculated. In one embodiment, the system can compute beat-to-beat HR from the R-R intervals, such as, for example, by subtracting the time between two successive R-peak intervals.

At block 525, heart rate variability is calculated. In one embodiment, the system can calculate HRV using the R-R interval values. The system can use time-domain approaches, frequency-domain approaches, and/or nonlinear approaches to calculate HRV. For time-domain approaches, the system can use root means square of successive differences (RMSSD) and the standard deviation of NN intervals (SDNN). RMSSD can include taking the root mean square of successive differences between consecutive R-peaks. SDNN can include taking the standard deviation between two consecutive normal R-peaks. The frequency-domain approach can include using the ratio between the low frequency (LF) and the high frequency (HF) values. For a nonlinear approach, the system can calculate HRV using Poincare plots, a method that can be used to detect the presence of oscillations in non-linear systems. In various embodiments, the system can vary the window size of the R-R interval time series data for calculating HRV from ~ 20 seconds to ~ 20 minutes or more to record respiratory events and sleep staging, respectively. The system can segment ECG beats according to R-peak values and store this data in a beat array for subsequent analysis.

At block 530, a pre-ejection period is calculated. The PEP may correspond to the delay between the R-peak and the AO point. In one embodiment, the PEP values are plotted on a graph. This graph can show the points at which an apnea event terminates for a user with obstructive sleep apnea. The increase in heart rate can cause an increase in cardiac inotropy, which can shorten the PEP. These measurements can also be displayed on the PEP graph. On such a graph, the PEP measurements dip at apnea termination (e.g., at the end of the respiratory disturbance), as shown by the arrows.

At block 535, noise estimation is calculated. In one embodiment, the system can be used to assess or determine peaks per beat. A classical PPG beat contains at most two discernable local maxima (one for the forward-traveling pulse wave, and one for the reflected wave). The system can flag a beat that contains three or more detectable peaks as potentially corrupted by artifacts based on the definition of classical PPG described previously herein. For the system, a time window that exceeds a certain number of "outlier" peaks (e.g., a configurable threshold number) can be considered noisy. The system can determine that a time window with a peak amplitude variance (e.g., peak heights modulating chaotically and drastically beat to beat) that meets or exceeds the threshold is noisy.

Figure 6:
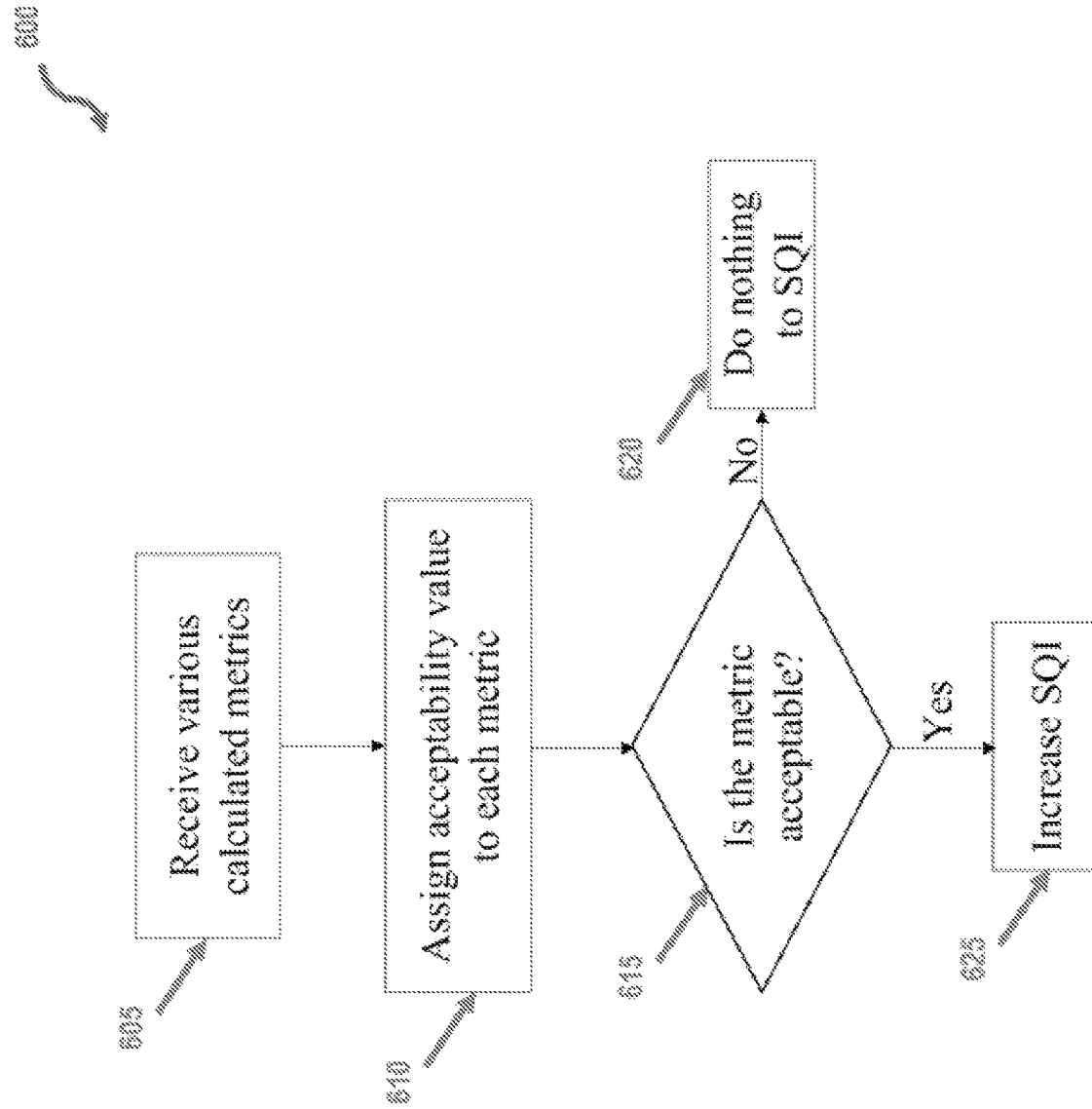
FIG. 6 is a flowchart describing the process to calculate signal quality index (SQI) according to various embodiments of the present disclosure.

FIG. 6 is a flowchart describing the process to calculate signal quality index (SQI) according to various embodiments of the present disclosure. In one embodiment, the system can combine various metrics to compute a composite SQI. These various metrics may include any of the variety of metrics previously discussed.

In one embodiment, the data collected by the PPG sensor can be compared with data collected by the ECG sensor to verify the accuracy of the data. In another embodiment, a multitude of other sensors can capture and determine a same vital statistic (e.g., a heart rate) such that if a particular sensor reads incorrect data (e.g., because the particular sensor shifted, was pushed, was bumped, encountered sweat or water, etc.), the measured vital statistic from another one of the other sensors can be used instead until the particular sensor is fixed or reads correctly. In one embodiment, the system removes the incorrect data, rather than the system fixing the sensors, which can be done as a step with computing the composite SQI.

The process begins at block 605 where a plurality of metrics are received. In one embodiment, the metrics may correspond to cardiodicity, red-IR cross-correlation, local distance, local variance, and/or pulse amplitude.

Then, at block 610, the metrics are given an "acceptability" value. Said another way, each individual quality metric may be assigned an "acceptable" threshold value (e.g., a predetermined threshold value, depending on the parameter).

At block 615, the system determines if the metric is acceptable based on the predetermined threshold value. If it is not acceptable, the method proceeds to block 620, and the SQI remains unchanged. If the metric is acceptable, the method proceeds to block 625 where the SQI is increased. In one embodiment, if the metric falls on the "accept" side of the threshold, the system can give a weighted "vote" toward the SQI. The system can then calculate the SQI as a weighted sum of all signal quality metrics' votes. The system may use this composite average of individual, orthogonal quality metrics calculated on a window-by-window basis such that it can be expressed as a timeseries and used to reject certain regions of interest within each record that do not meet a predefined SQI threshold.

The system can calculate the SQI for PPG in various ways. Template matching is the process of matching small parts or portions of a signal to a template signal. A good-quality PPG may generally appear stable and consistent in morphology at relatively short timescales. Morphology may include the study and description of geometrical images or signals. The system can capture this behavior quantitatively by comparing individual PPG beats to a template, which can be defined as the ensemble average beat in a given time window sized, for example, to contain at least 5 beats, at least 10 beats, at least 15 beats, or some other size. The system can do this to ensure "consensus" when averaging. The system may quantify the beat-to-beat variance by calculating the standard deviation around the local ensemble average ("local variance"). The system can also capture local signal consistency measurements by computing the "distance" between the individual beat and its local template ("local distance"). The system can determine "distance" by computing via dynamic time warping, cross-correlation, cosine similarity, coherence, or any other metric that compares two or more signals. For a peak-to-peak pulsatile amplitude, the system can extract the AC amplitude on a beat-to-beat basis. In various embodiments, if the system records high pulse amplitudes, this can correspond to a high signal-to-noise ratio (SNR) PPG.

The system can be used to assess or determine peaks per beat. A classical PPG beat contains at most two discernable local maxima (one for the forward-traveling pulse wave, and one for the reflected wave). The system can flag a beat that contains 3 or more detectable peaks as potentially corrupted by artifacts based on the definition of classical PPG described previously herein. For the system, a time window that exceeds a certain number of "outlier" peaks (e.g., a configurable threshold number) can be considered noisy. The system can determine that a time window with a peak amplitude variance (e.g., peak heights modulating chaotically and drastically beat to beat) that meets or exceeds the threshold is noisy.

A high-quality PPG signal can contain physiologically expected information (e.g., signal in the cardiac frequency band) and little else otherwise (e.g. artifact). For the system to determine the strength of the cardiac component of the PPG, it can segment the time windows, containing at least 5 beats, and can compute a normalized autocorrelation for each window. The term "cardiodicity" (periodicity at the dominant cardiac frequency) refers to the highest autocorrelation peak in the cardiac band (0.5-2.5 Hz), if one exists.

The system can use a red and IR LED along with a sensor to measure PPG over the desired tissue area. In various embodiments, the system may illuminate the same location with both LED's, which can illuminate the same volume of blood during each pulse. The system can consider this and determine that the cross-correlation between each channel may be high (ideally=1), and use this information to treat disparities between channels as the consequence of artifacts.

The ideal PPG signal can be characterized by high pulsatile amplitude, high perfusion index, low noise, high beat-wise repeatability, low beat-wise variance, and high cardiac frequency content. The system can combine the previously describe metrics to compute a composite signal quality index (SQI). For the system to calculate SQI, each individual quality metric (e.g., cardiodicity, red-IR cross-correlation, local distance, local variance, pulse amplitude) may be assigned an "acceptable" threshold value. As stated above, if the metric falls on the "accept" side of the threshold, the system can give a weighted "vote" toward the SQI. The system can then calculate the SQI as a weighted sum of all signal quality metrics' votes. The system may use this composite average of individual, orthogonal quality metrics calculated on a window-by-window basis such that it can be expressed as a timeseries and used to reject certain regions of interest within each record that do not meet a predefined SQI threshold. In other words, if the metrics are given an acceptable value at two instances, it is known that the metrics are high quality. If the metrics are only given one acceptable value, the metrics should be tested again and calculated for acceptability. If the metrics do not meet an acceptable threshold, the metrics should not be used. In one embodiment, the quality and fidelity of the calculated SpO2 are indexed by computing a normalized cross-correlation or Pearson's correlation coefficient between pulsatile red and IR signals within a time window of up to 10 seconds in length.

The system can calculate the SQI for SCG in the same or similar way that the SQI is computed for the PPG, except with only a subset of signal quality metrics getting a vote (e.g., peak-to-peak amplitude, local distance, local variance, cardiodicity). The system can calculate the SQI for ECG in the same way SQI is computed for the PPG, except with only a subset of signal quality metrics getting a vote (e.g., peak-to-peak amplitude, local distance, local variance, cardiodicity).

Figure 7:
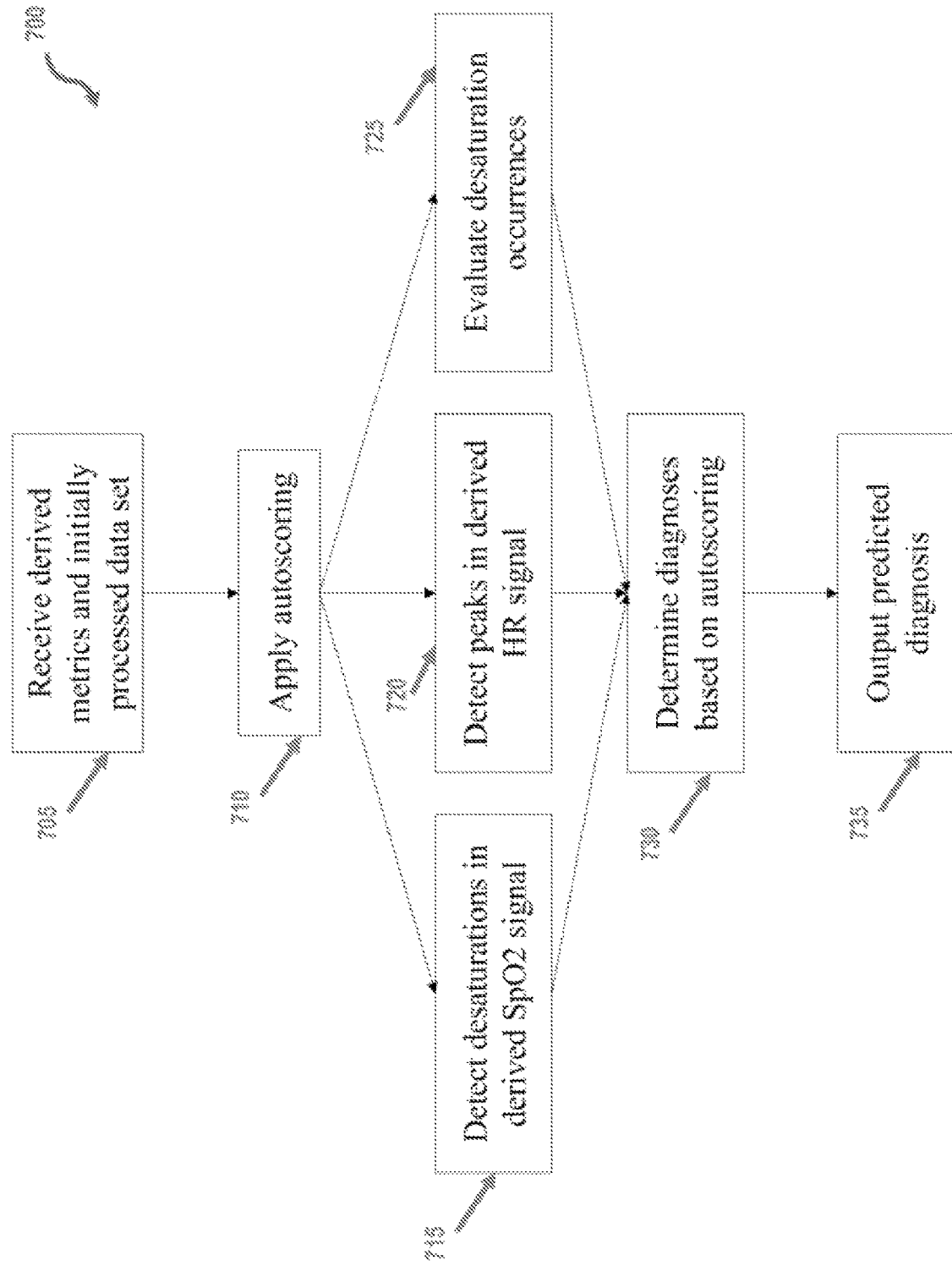
FIG. 7 is a flowchart describing the process to use autoscoring to predict a diagnosis according to various embodiments of the present disclosure.

FIG. 7 is a flowchart describing the process to use autoscoring to predict a diagnosis according to various embodiments of the present disclosure. The flowchart begins at block 705 where derived metrics and the initially processed data set are received. In one embodiment, the derived metrics are those that were created at block 415 in FIG. 4, and the initially processed data set is that which was outputted at block 435 in FIG. 4.

At block 710, the system receives data for autoscoring. In one or more embodiments, the system's autoscore, which is the method by which the system can detect respiratory disturbances like apneas and hypopneas automatically from derived parameters like HR, SpO2, etc., can be influenced by various scoring guidelines, such as, for example, the American Academy of Sleep Medicine (AASM) scoring guidelines. The autoscore can represent a baseline attempt that leverages a limited number of signals that could be utilized by a sleep technician scoring a sleep study. The system may incorporate more sophisticated methodologies, such as machine learning, for autoscoring.

The system can detect changes from baseline in given physiological signal. The system can determine if changes meet a threshold difference and threshold duration that would qualify it as event-worthy. Moreover, the system can determine if event-worthy changes in the defined parameters occur in the proper order and proximity in time relative to one another. The system can sum the valid event-worthy responses in multiple signals to form an event likelihood index.

One common series of physiological phenomena occurs during the incidence of a sleep disordered breathing event: (1) a decrease in respiratory effort, (2) a decrease in blood oxygenation, (3) an arousal from sleep, which may follow one another in numerical order. In some embodiments, the system can detect three physiological time series derived during a feature extraction to represent the following three phenomena: (1) respiratory effort from low-frequency accelerometry, (2) SpO2 calculated from red/IR PPG, and (3) heart rate calculated from ECG. The system can detect decreases in respiratory effort as a trough in the amplitude envelope of the respiratory accelerometer signal. The amplitude envelope is a representation of the change in a sound's energy over time, which is detected from the heart sounds. The mediolateral axis of the accelerometer can provide the most sensitive measurement of respiratory effort relative to a standard RIP belt, though any combination of the three axes by the system can be used. In one embodiment, the microcontroller of the patch device 100 can compute a Euclidean distance of the three-axis accelerometer sample-by-sample. The Euclidean distance can be used to calculate a distance between each point of the three-axis accelerometer to determine a three-dimensional distance between various locations. More specifically, the system can determine the distance between data points in a three-dimensional plane. The device can arrange the SCG, PCG, and KCG data using R-peaks of individual heartbeats and store these values into beat arrays for subsequent analysis.

To ensure even minor contractions of the respiratory effort may be considered, the system can capture envelopes (since respiratory effort may remain relatively high even during obstructed breathing) and trough detection threshold can be set at a conservative value (normally ~80% of the local baseline value). The system can detect troughs with minimal spacing in between (10 seconds), consistent with AASM guidelines that airway obstructions manifest for at least 10 seconds for it to be considered an apnea or hypopnea. The system can exclude segments based on SCG or ECG SQI if respiratory effort appear highly chaotic due to motion artifacts. Additionally, in various embodiments, the detection of a respiratory disturbance is gated by sleep stage as determined by a combination of information regarding motion and cardiovascular state. In some embodiments, the information regarding cardiovascular state comprises time- and frequency-domain features of heart rate computed in windows of length 30 seconds or greater, and the windowed features are used as inputs to a supervised machine learning model which renders time-varying sleep stage (wake, REM, non-REM) estimations in windows of length 30 seconds or greater.

At block 715, the system can detect desaturations as troughs in the derived SpO2 signal. Desaturations can imply the number of times the oxygen level in the blood drops below baseline. The system may ensure the SpO2 nadirs (e.g., the lowest oxygen saturation values a particular patient drops to) have a prominence of 3% (or some other threshold) or greater to qualify as an event (4% depending on the insurance provider), which can be consistent with AASM scoring guidelines. The system can require that the SpO2 nadirs be spaced at least 10 seconds apart to avoid over-detection of spurious troughs. The system can correct SpO2 signals by subtracting baseline wander if the baseline shifts in SpO2 are apparent and problematic (such as can be the case when a subject changes positions). If SpO2 appears highly chaotic due to poor PPG signal quality, the system can exclude segments based on PPG SQI, and/or multiple SpO2 algorithms can be averaged together to form a "consensus" SpO2.

At block 720, the system detects arousals as peaks in the HR signal (e.g. tachycardia). For tachycardia to be considered, the system can ensure a deviation by 3 beats per minute (BPM) or greater is detected from the baseline HR. In some embodiments, the system can detect HR peaks as long as the peaks are at least 10 seconds apart. The system can exclude segments based on ECG SQI if HR appears highly chaotic due to motion artifact.

At block 725, the system evaluates desaturation occurrences. In one embodiment, the system can scrutinize all respiratory contractions, desaturations, and tachycardia's to see if they occur in the predetermined sequence. The system can mark a desaturation occurrence as a valid effort-desaturation dyad if the desaturation occurs within a predetermined timeframe after a respiratory contraction. The system can mark a tachycardia occurrence as a valid desaturation-arousal dyad if it occurs within a certain timeframe after a desaturation. If the system can detect that both dyads happened in sequence, it is deemed a valid event triad and is tallied as a respiratory disturbance (which can be used for either an apnea or a hypopnea). If the system can detect that only one dyad occurred, the system can label the sequence as a possible respiratory disturbance (with a likelihood percentage computed and assigned based on the SQI of each contributing signal).

At block 730, the system determines a predicted diagnosis based on autoscoring. In one embodiment, the autoscoring may provide an indication of what particular diagnosis may be applicable based on the patent data and metrics described above. For example, if the derived metrics that have been autoscored show an abnormal breathing pattern, then a predicted diagnosis may be of sleep apnea.

At block 735, the system outputs the predicted diagnosis. In one embodiment, this predicted diagnosis may be used by a physician to provide a patient with medications or therapies that may remedy or repair the diagnosis. In various embodiments, the predicted diagnosis may be out to a display, notification (including, for example, text message, email, system notification, portal notification, portal message), or the like. In at least one embodiment, the system may be configured to modify at least one display to display or otherwise convey the predicted diagnosis.

Figure 8:
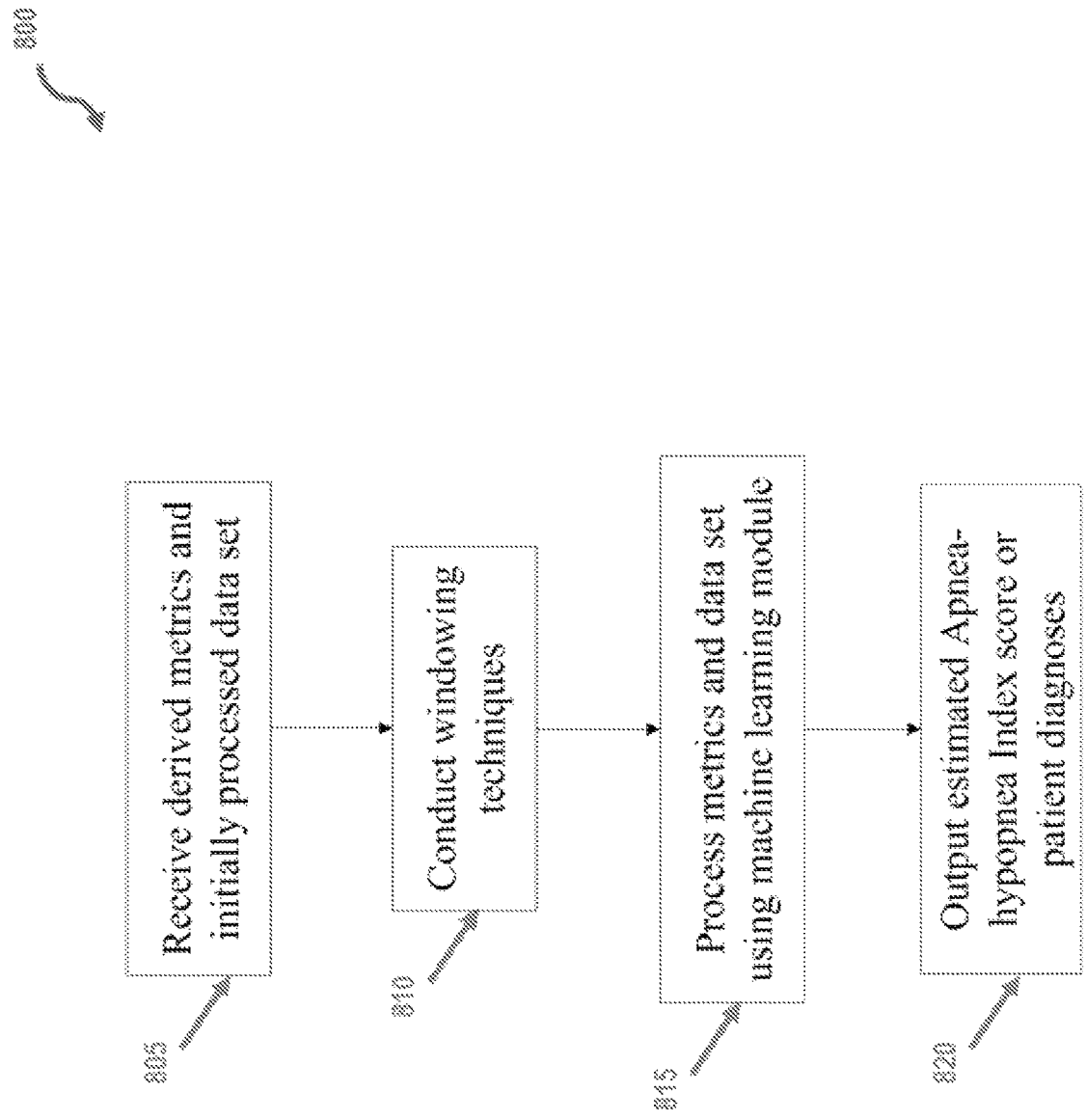
FIG. 8 is a flowchart showing an exemplary machine learning process according to various embodiments of the present disclosure.

FIG. 8 is a flowchart showing an exemplary machine learning process according to various embodiments of the present disclosure. The flowchart begins at block 805 where derived metrics and the initially processed data set are received. In one embodiment, the derived metrics are those that were created at block 415 in FIG. 4 and the initially processed data set is that which was output at block 435 in FIG. 4.

At block 810, windowing techniques are applied to the metrics and data set. A window may be adjusted using a variety of different techniques to create different metrics. According to at least one embodiment, window functionality comprises three steps: detection of an overlap between a plurality of windows, application of operations to each of the windows, and development of a windowed feature time series. The operations that may be applied vary and are discussed in the following paragraphs.

In one embodiment, periodicity in a respiration band is calculated. Normalized autocorrelation is applied to the windows. This is done to detect in-band peaks. In another embodiment, peak orderliness or predictable amplitude modulation is calculated. Peaks on the developed graphs are detected. For example, hypopnea or respiratory decoupling of PPG may be detected at these peaks. A polynomial fit (e.g., (y=mx+b), (y=mx$^2$+bx+c)) is then applied to these graphs with detected peaks. From there, a goodness-of-fit ($R^2$/RMSE) calculation is made.

In yet another embodiment, signal stochasticity is calculated. Initially, activity is calculated at each window: var(x). The mobility is then calculated: the square root of (var(x')/activity. Finally, the complexity is calculated: the square root of (var (x")/var (x'))/mobility. According to at least one embodiment, the dominance of suitable frequency is detected, otherwise called fast Fourier transform (FFT) peakedness. Initially, the FFT peak is calculating using a plot. The crest factor is then calculated by taking $P_{MAX}$ divided by $P_{RMS}$.

According to at least one embodiment, the system can create a DC data set by using a moving average filter of a particular window size (e.g., approximately between 5-30 seconds). The system can apply the moving average filter (e.g., to a time domain signal) to reduce short term fluctuations and accentuate long term patterns. The AC component can include all the data that was not filtered out by the moving average filter.

In various embodiments, the system can vary the window size of the R-R interval time series data for calculating heart rate variability (HRV) from ~ 20 seconds to ~ 20 minutes or more to record respiratory events and sleep staging, respectively. The system can apply a moving-window (e.g., interval-based) ensemble averaging to the beat arrays constructed for the ECG, red PPG, IR PPG, SCG, PCG, and KCG. As an example, the system can calculate the moving window ensemble average to the beat arrays.

At block 815, the metrics and data set are processed using a machine learning module. In one embodiment, the machine learning module is machine learning module 320 in FIG. 3. In one embodiment, machine learning is used for autoscoring. In particular embodiments, the first step in the construction of a "grey box" machine learning (ML) based autoscore for detecting sleep disordered breathing events and estimating an Apnea-hypopnea Index (AHI) is to generate a set of features to serve as inputs (predictors) to the algorithm. In one or more embodiments, the term "grey box" refers to the limited, but in some cases non-zero, ability to change various aspects of the machine learning system. In various embodiments, to make the model more interpretable to a clinical audience, the algorithm is grounded in physiologically relevant features derived from each of the time-series signals collected by the system. Input features for the ML autoscore may derive from time-series signals (e.g., ECG, PPG, SCG, PCG) and derived parameters (e.g., SpO2, HR, HRV, PEP, noise estimation). These time-series feature substrates may include, but are not limited to:

PPG
    Red and IR
    Raw, AC, DC, and digitally filtered
ECG
    Raw, AC, DC, and digitally filtered
Raw accelerometer
    x-, y-, and z-axes
Respiratory effort
    x-, y-, and z-axes
Respiratory rate
Body position
SCG
    x-, y-, and z-axes
    Euclidean norm
    Amplitude-enveloped
PCG
    x-, y-, and z-axes
    Euclidean norm
    Amplitude-enveloped
HR
    HRV
    RMSSD
    O SDNN
    LF/HF ratio
    Poincare plot dimensions
SpO2
    All methods as described previously (B2B, EWMA, FFT, ENV, LSQ, INT, PKS)
SCG fiducial point-based metrics (both beat-by-beat and locally averaged)
    Pre-ejection period (PEP)
    Left ventricular ejection time (L VET)
    Isovolumetric contraction time (ICT)
    Isovolumetric relaxation time (IR T)
    Diastolic filling time (DFT)
    Aortic opening (AO) amplitude
    Isovolumetric contraction point (ICP) amplitude
    Isovolumetric relaxation point (IRP) amplitude
    Systolic peak complex energy
    Diastolic peak complex energy
PCG fiducial point-based metrics (both beat-by-beat and locally averaged)
    First heart sound (S1) amplitude
    S1 delay
    Second heart sound (S2) amplitude
    S2 delay
    S1/S2 amplitude ratio
    S1/S2 interval
PPG-based metrics (both beat-by-beat and locally averaged)
    Pulse arrival time (PAT)
    Pulse transit time (PTT) (PAT from PPG minus PEP from SCG)
    Reflection index
    Augmentation index
    Pulse amplitude
    Perfusion index
    2nd-derivative PPG (SDPPG) local optima
    Point of maximal acceleration (PMA)
KCG-based metrics (both beat-by-beat and locally averaged)
    Linear kinetic energy
    Linear force
Signal quality metrics
    Local distance of PPG, ECG, and SCG
    Local autocorrelation of PPG, ECG, and SCG
    Red-IR PPG cross-correlation
    PPG cardiodicity
    Composite signal quality index (SQI) of PPG, ECG, and SCG
Output metrics (labels)
    Manual scores from registered sleep technician, primarily the union of
        Central apnea
        Obstructive apnea
        Mixed apnea
        Hypopnea At block 820, an estimated API score or patient diagnoses are outputted. These outputs can provide a physician with an understanding of the patient's condition and advise on the diagnosis to further remedy any issues.

Any logic or application described herein may be implemented and structured in a variety of ways. For example, one or more applications described may be implemented as modules or components of a single application. Further, one or more applications described herein may be executed in shared or separate computing systems or a combination thereof. For example, more than one application may execute in the same computing system, or in multiple computing systems in the same computing environment. Additionally, it is understood that terms such as "application," "service," "system," "engine," "module," and so on may be interchangeable and are not intended to be limiting.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

The invention claimed is:

1. A cardiorespiratory analysis system comprising:
a patch comprising:
a photoplethysmography (PPG) sensor;
a 3-axis accelerometer;
an electrocardiogram (ECG) sensor;
a microcontroller wired to the PPG sensor, the 3-axis accelerometer, and the ECG sensor;
an adhesive layer configured to adhere to skin of a chest of a patient; and
one or more rigid components connected to the adhesive layer, wherein:
the PPG sensor passes through the adhesive layer and is coupled to the one or more rigid components via a flexible substrate, thereby isolating the PPG sensor from the one or more rigid components; and
an air gap exists between a lower surface of the adhesive layer and a lower surface of the PPG sensor such that the patch applies a compressive force to the PPG sensor when the lower surface of the adhesive layer and lower surface of the PPG sensor are in contact with the chest of the patient thereby improving signal quality of the PPG sensor; and
a computing system comprising at least one processor and configured for:
parsing sensor data received from the microcontroller into time series data associated with one or more data points of the sensor data, the one or more data points comprising:
x axis data, y axis data, and z axis data derived from the 3-axis accelerometer;
red data and IR data derived from the PPG sensor; and
amplitude and frequency data derived from the ECG sensor;
determining heart rate from the amplitude and frequency data from the ECG sensor;
extracting data representing one or more heart beats from the red data and IR data;
computing verified red data and verified IR data by comparing the one or more heart beats from the red data and the IR data and the amplitude and frequency data from the ECG sensor to verify accuracy of the red data and the IR data, wherein comparing the one or more heart beats from the red data and the IR data and the amplitude and frequency data from the ECG sensor comprises synchronizing one or more locations on an ECG waveform and one or more locations on a PPG waveform via pulse transit time; and
deriving a plurality of oxygen saturation (SpO2) data points based on the verified red data and the verified IR data.

2. The cardiorespiratory analysis system of claim 1, wherein deriving the plurality of SpO2 data points based on verified red data and verified IR data comprises determining a plurality of optical ratios by:
splitting the verified red data into red AC data and red DC data;
splitting the verified IR data into IR AC data and IR DC data; and
computing:

$$R = \frac{AC_{rms\ RED} / DC_{rms\ RED}}{AC_{rms\ IR} / AC_{rms\ IR}}$$

wherein:
R is an optical ratio;
$AC_{rms}$ RED is a root mean square of the red AC data;
$DC_{rms}$ RED is a root mean square of the red DC data;
$AC_{rms}$ IR is a root mean square of the IR AC data; and
$DC_{rms}$ IR is a root mean square of the IR DC data.

3. The cardiorespiratory analysis system of claim 2, wherein the computing system is further configured for removing baseline wander from the red DC signal and the IR DC signal by removing a particular range of values from the red DC signal and the IR DC signal based on a number of baseline data shifts included in the ECG data.

4. The cardiorespiratory analysis system of claim 3, wherein the ECG sensor includes two ECG electrodes.

5. A cardiorespiratory analysis system comprising:
a patch comprising:
a photoplethysmography (PPG) sensor;
an electrocardiogram (ECG) sensor;
a microcontroller wired to the PPG sensor and the ECG sensor;
an adhesive layer configured to adhere to skin of a chest of a patient; and
one or more rigid components connected to the adhesive layer, wherein:
the PPG sensor passes through the adhesive layer; and
an air gap exists between a lower surface of the adhesive layer and a lower surface of the PPG sensor such that the patch applies a compressive force to the PPG sensor when the lower surface of the adhesive layer and lower surface of the PPG sensor are in contact with the chest of the patient thereby improving signal quality of the PPG sensor; and
a computing system comprising at least one processor and configured for:
parsing sensor data received from the microcontroller into time series data associated with one or more data points of the sensor data, the one or more data points comprising:
red data and IR data derived from the PPG sensor; and
amplitude and frequency data derived from the ECG sensor;
determining heart rate from the amplitude and frequency data from the ECG sensor;
extracting data representing one or more heart beats from the red data and IR data;
computing verified red data and verified IR data by comparing the one or more heart beats from the red data and the IR data and the amplitude and frequency data from the ECG sensor to verify accuracy of the red data and the IR data; and
deriving a plurality of oxygen saturation (SpO2) data points based on the verified red data and the verified IR data.

6. The cardiorespiratory analysis system of claim 5, wherein the PPG sensor is coupled to the one or more rigid components via a flexible substrate, thereby isolating the PPG sensor from the one or more rigid components.

7. The cardiorespiratory analysis system of claim 6, wherein deriving the plurality of SpO2 data points based on verified red data and verified IR data comprises determining a plurality of optical ratios by:
  splitting the verified red data into red AC data and red DC data;
  splitting the verified IR data into IR AC data and IR DC data; and
  computing:

$$R = \frac{AC_{rms\,RED} / DC_{rms\,RED}}{AC_{rms\,IR} / AC_{rms\,IR}}$$

wherein:
  R is an optical ratio;
  $AC_{rms}$ RED is a root mean square of the red AC data;
  $DC_{rms}$ RED is a root mean square of the red DC data;
  $AC_{rms}$ IR is a root mean square of the IR AC data; and
  $DC_{rms}$ IR is a root mean square of the IR DC data.

8. The cardiorespiratory analysis system of claim 7, wherein the computing system is further configured for removing baseline wander from the red DC signal and the IR DC signal by removing a particular range of values from the red DC signal and the IR DC signal based on a number of baseline data shifts included in the ECG data.

9. The cardiorespiratory analysis system of claim 8 further comprising a 3-axis accelerometer.

10. The cardiorespiratory analysis system of claim 9, wherein the one or more data points further comprise x axis data, y axis data, and z axis data derived from the 3-axis accelerometer.

11. The cardiorespiratory analysis system of claim 10, wherein the ECG sensor includes two ECG electrodes.

12. The cardiorespiratory analysis system of claim 5, wherein comparing the one or more heart beats from the red data and the IR data and the amplitude and frequency data from the ECG sensor comprises synchronizing one or more locations on an ECG waveform and one or more locations on a PPG waveform via pulse transit time.

13. A cardiorespiratory analysis system comprising:
  a patch comprising:
    a photoplethysmography (PPG) sensor;
    an electrocardiogram (ECG) sensor;
    a microcontroller wired to the PPG sensor and the ECG sensor;
    an adhesive layer configured to adhere to skin of a chest of a patient; and
    one or more rigid components connected to the adhesive layer, wherein the PPG sensor passes through the adhesive layer and is coupled to the one or more rigid components via a flexible substrate, thereby isolating the PPG sensor from the one or more rigid components and improving signal quality of the PPG sensor, and wherein an air gap exists between a lower surface of the adhesive layer and a lower surface of the PPG sensor such that the patch applies a compressive force to the PPG sensor when the lower surface of the adhesive layer and lower surface of the PPG sensor are in contact with the chest of the patient; and
  a computing system comprising at least one processor and configured for:
    parsing sensor data received from the microcontroller into time series data associated with one or more data points of the sensor data, the one or more data points comprising:
      red data and IR data derived from the PPG sensor; and
      amplitude and frequency data derived from the ECG sensor;
    determining heart rate from the amplitude and frequency data from the ECG sensor;
    extracting data representing one or more heart beats from the red data and IR data;
    computing verified red data and verified IR data by comparing the one or more heart beats from the red data and the IR data and the amplitude and frequency data from the ECG sensor to verify accuracy of the red data and the IR data; and
    deriving a plurality of oxygen saturation (SpO2) data points based on the verified red data and the verified IR data.

14. The cardiorespiratory analysis system of claim 13, wherein deriving the plurality of SpO2 data points based on verified red data and verified IR data comprises determining a plurality of optical ratios by:
  splitting the verified red data into red AC data and red DC data;
  splitting the verified IR data into IR AC data and IR DC data; and
  computing:

$$R = \frac{AC_{rms\,RED} / DC_{rms\,RED}}{AC_{rms\,IR} / AC_{rms\,IR}}$$

wherein:
  R is an optical ratio;
  $AC_{rms}$ RED is a root mean square of the red AC data;
  $DC_{rms}$ RED is a root mean square of the red DC data;
  $AC_{rms}$ IR is a root mean square of the IR AC data; and
  $DC_{rms}$ IR is a root mean square of the IR DC data.

15. The cardiorespiratory analysis system of claim 14, wherein the computing system is further configured for removing baseline wander from the red DC signal and the IR DC signal by removing a particular range of values from the red DC signal and the IR DC signal based on a number of baseline data shifts included in the ECG data.

16. The cardiorespiratory analysis system of claim 15 further comprising a 3-axis accelerometer.

17. The cardiorespiratory analysis system of claim 16, wherein the one or more data points further comprise x axis data, y axis data, and z axis data derived from the 3-axis accelerometer.

18. The cardiorespiratory analysis system of claim 17, wherein the ECG sensor includes two ECG electrodes.

19. The cardiorespiratory analysis system of claim 18, wherein comparing the one or more heart beats from the red data and the IR data and the amplitude and frequency data from the ECG sensor comprises synchronizing one or more locations on an ECG waveform and one or more locations on a PPG waveform via pulse transit time.

\* \* \* \* \*